(12) United States Patent
Gerber

(10) Patent No.: US 10,561,835 B2
(45) Date of Patent: Feb. 18, 2020

(54) IMPLANTABLE MEDICAL LEAD WITH THREADED FIXATION

(71) Applicant: Medtronic, Inc., Minneapolis, MN (US)

(72) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/528,089

(22) Filed: Jul. 31, 2019

(65) Prior Publication Data
US 2019/0351218 A1   Nov. 21, 2019

Related U.S. Application Data

(63) Continuation of application No. 11/591,171, filed on Oct. 31, 2006, now abandoned.

(51) Int. Cl.
*A61N 1/05* (2006.01)
*A61N 1/36* (2006.01)

(52) U.S. Cl.
CPC ......... *A61N 1/0529* (2013.01); *A61N 1/0534* (2013.01); *A61N 1/0558* (2013.01);
(Continued)

(58) Field of Classification Search
CPC ..... A61N 1/0529; A61N 1/0558; A61N 1/057
See application file for complete search history.

(56) References Cited

U.S. PATENT DOCUMENTS

| 3,646,940 A | 3/1972 | Timm et al. |
| 3,857,399 A | 12/1974 | Zacouto |

(Continued)

FOREIGN PATENT DOCUMENTS

| EP | 0584525 | 3/1994 |
| EP | 1374945 | 1/2004 |

(Continued)

OTHER PUBLICATIONS

Notification of Transmittal of the International Preliminary Report on Patentability for PCT Application No. PCT/US2007 /001962 dated Feb. 10, 2009 (11 pgs.).
(Continued)

*Primary Examiner* — William J Levicky
(74) *Attorney, Agent, or Firm* — Shumaker & Sieffert P.A.

(57) ABSTRACT

The disclosure is directed to securing electrodes of a medical lead adjacent to a target tissue site. The medical lead may include one or more threaded fixation structures disposed circumferentially about the outer surface of the lead body, or elongated member, that resembles a "screw" or "auger." During implantation, a clinician may rotate the entire lead to "screw" the lead into the tissue of the patient until electrodes of the lead reside adjacent to a target tissue. In this manner, the threaded fixation structure secures the lead within the patient to resist lead migration and improper therapy and provide a fine adjustment for depth of placement. The threaded fixation structure may be disposed on a portion of the lead proximal to or distal to the electrodes of the lead or over the portion of the lead that includes the electrodes.

22 Claims, 14 Drawing Sheets

(52) U.S. Cl.
CPC ............ *A61N 1/057* (2013.01); *A61N 1/0536* (2013.01); *A61N 1/3605* (2013.01)

(56) References Cited

U.S. PATENT DOCUMENTS

| | | | |
|---|---|---|---|
| 4,019,518 A | 4/1977 | Maurer et al. | |
| 4,044,774 A | 8/1977 | Corbin et al. | |
| 4,142,530 A | 3/1979 | Wittkampf | |
| 4,340,062 A | 7/1982 | Thompson et al. | |
| 4,341,226 A | 7/1982 | Peters | |
| 4,366,493 A | 12/1982 | Braslau et al. | |
| 4,379,459 A | 4/1983 | Stein | |
| 4,475,560 A | 10/1984 | Tarjan et al. | |
| 4,476,868 A | 10/1984 | Thompson | |
| 4,550,737 A * | 11/1985 | Osypka ................ | A61N 1/057 607/127 |
| 4,556,063 A | 12/1985 | Thompson et al. | |
| 4,558,702 A | 12/1985 | Barreras et al. | |
| 4,716,888 A | 1/1988 | Wesner | |
| 4,744,371 A | 5/1988 | Harris | |
| 4,821,723 A | 4/1989 | Baker, Jr. et al. | |
| 4,841,971 A | 6/1989 | Hess | |
| 4,997,431 A | 3/1991 | Isner et al. | |
| 4,998,975 A | 3/1991 | Cohen et al. | |
| 5,009,229 A | 4/1991 | Grandjean et al. | |
| 5,071,407 A | 12/1991 | Termin et al. | |
| 5,131,388 A | 7/1992 | Pless et al. | |
| 5,144,949 A | 9/1992 | Olson | |
| 5,165,403 A | 11/1992 | Mehra | |
| 5,241,957 A | 9/1993 | Camps et al. | |
| 5,312,453 A | 5/1994 | Shelton et al. | |
| 5,314,430 A | 5/1994 | Bardy | |
| 5,354,316 A | 10/1994 | Keimel | |
| 5,374,287 A | 12/1994 | Rubin | |
| 5,423,884 A | 6/1995 | Nyman et al. | |
| 5,456,708 A | 10/1995 | Doan | |
| 5,487,758 A | 1/1996 | Hoegnelid et al. | |
| 5,496,360 A | 3/1996 | Hoffmann et al. | |
| 5,531,781 A | 7/1996 | Alferness et al. | |
| 5,545,186 A | 8/1996 | Olson et al. | |
| 5,554,139 A | 9/1996 | Okajima | |
| 5,683,446 A | 11/1997 | Gates | |
| 5,690,693 A | 11/1997 | Wang et al. | |
| 5,702,428 A | 12/1997 | Tippey et al. | |
| 5,702,431 A | 12/1997 | Wang et al. | |
| 5,728,140 A | 3/1998 | Salo et al. | |
| 5,735,887 A | 4/1998 | Barreras, Sr. et al. | |
| 5,741,316 A | 4/1998 | Chen et al. | |
| 5,865,842 A | 2/1999 | Knuth et al. | |
| 5,876,423 A | 3/1999 | Braun | |
| 5,948,015 A | 9/1999 | Hess et al. | |
| 6,027,456 A | 2/2000 | Feler et al. | |
| 6,035,237 A | 3/2000 | Schulman et al. | |
| 6,049,736 A | 4/2000 | Stewart et al. | |
| 6,052,624 A | 4/2000 | Mann | |
| 6,055,456 A | 4/2000 | Gerber | |
| 6,057,513 A | 5/2000 | Ushikoshi et al. | |
| 6,067,474 A | 5/2000 | Schulman et al. | |
| 6,076,017 A | 6/2000 | Taylor et al. | |
| 6,078,840 A | 6/2000 | Stokes | |
| 6,161,047 A | 12/2000 | King et al. | |
| 6,172,556 B1 | 1/2001 | Prentice | |
| 6,178,353 B1 | 1/2001 | Griffith et al. | |
| 6,191,365 B1 | 2/2001 | Avellanet | |
| 6,208,894 B1 | 3/2001 | Schulman et al. | |
| 6,212,431 B1 | 4/2001 | Hahn et al. | |
| 6,221,513 B1 | 4/2001 | Lasater | |
| 6,246,911 B1 | 6/2001 | Seligman | |
| 6,249,703 B1 | 6/2001 | Stanton et al. | |
| 6,263,250 B1 | 7/2001 | Skinner | |
| 6,265,789 B1 | 7/2001 | Honda et al. | |
| 6,306,100 B1 | 10/2001 | Prass | |
| 6,315,721 B2 | 11/2001 | Schulman et al. | |
| 6,354,991 B1 | 3/2002 | Gross et al. | |
| 6,360,750 B1 | 3/2002 | Gerber et al. | |
| 6,393,325 B1 | 5/2002 | Mann et al. | |
| 6,405,091 B1 | 6/2002 | Vachon et al. | |
| 6,438,423 B1 | 8/2002 | Rezai et al. | |
| 6,442,434 B1 | 8/2002 | Zarinetchi et al. | |
| 6,466,817 B1 | 10/2002 | Kaula et al. | |
| 6,505,075 B1 | 1/2003 | Weiner | |
| 6,516,227 B1 | 2/2003 | Meadows et al. | |
| 6,584,355 B2 | 6/2003 | Stessman | |
| 6,600,954 B2 | 7/2003 | Cohen et al. | |
| 6,607,511 B2 | 8/2003 | Halseth et al. | |
| 6,609,031 B1 | 8/2003 | Law et al. | |
| 6,609,032 B1 | 8/2003 | Woods et al. | |
| 6,652,449 B1 | 11/2003 | Gross et al. | |
| 6,662,051 B1 | 12/2003 | Eraker et al. | |
| 6,721,603 B2 | 4/2004 | Zabara et al. | |
| 6,735,474 B1 | 5/2004 | Loeb et al. | |
| 6,745,077 B1 | 6/2004 | Griffith et al. | |
| 6,792,314 B2 | 9/2004 | Byers et al. | |
| 6,792,318 B2 | 9/2004 | Chitre et al. | |
| 6,809,701 B2 | 10/2004 | Amundson et al. | |
| 6,836,684 B1 | 12/2004 | Rijkhoff et al. | |
| 6,847,849 B2 | 1/2005 | Mamo et al. | |
| 6,892,098 B2 | 5/2005 | Ayal et al. | |
| 6,895,280 B2 | 5/2005 | Meadows et al. | |
| 6,896,651 B2 | 5/2005 | Gross et al. | |
| 6,901,287 B2 | 5/2005 | Davis et al. | |
| 6,941,171 B2 | 9/2005 | Mann et al. | |
| 6,944,507 B2 | 9/2005 | Froberg et al. | |
| 6,971,393 B1 | 12/2005 | Mamo et al. | |
| 6,989,200 B2 | 1/2006 | Byers et al. | |
| 6,990,376 B2 | 1/2006 | Tanagho et al. | |
| 6,999,819 B2 | 2/2006 | Swoyer et al. | |
| 7,051,419 B2 | 5/2006 | Schrom et al. | |
| 7,054,689 B1 | 5/2006 | Whitehurst et al. | |
| 7,069,081 B2 | 6/2006 | Biggs et al. | |
| 7,081,113 B2 | 7/2006 | Sutton | |
| 7,127,298 B1 | 10/2006 | He et al. | |
| 7,142,925 B1 | 11/2006 | Bhadra et al. | |
| 7,146,219 B2 | 12/2006 | Sieracki et al. | |
| 7,151,914 B2 | 12/2006 | Brewer | |
| 7,167,749 B2 | 1/2007 | Biggs et al. | |
| 7,177,690 B2 | 2/2007 | Woods et al. | |
| 7,177,698 B2 | 2/2007 | Klosterman et al. | |
| 7,181,286 B2 | 2/2007 | Sieracki et al. | |
| 7,187,978 B2 | 3/2007 | Malek et al. | |
| 7,191,005 B2 | 3/2007 | Stessman | |
| 7,212,110 B1 | 5/2007 | Martin et al. | |
| 7,225,032 B2 | 5/2007 | Schmeling et al. | |
| 7,231,254 B2 | 6/2007 | DiLorenzo | |
| 7,234,853 B2 | 6/2007 | Givoletti | |
| 7,245,972 B2 | 7/2007 | Davis | |
| 7,286,880 B2 | 10/2007 | Olson et al. | |
| 7,305,268 B2 | 12/2007 | Gliner et al. | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,328,068 B2 | 2/2008 | Spinelli et al. | |
| 7,330,764 B2 | 2/2008 | Swoyer et al. | |
| 7,359,751 B1 | 4/2008 | Erickson et al. | |
| 7,369,894 B2 | 5/2008 | Gerber | |
| 7,386,348 B2 | 6/2008 | North et al. | |
| 7,387,603 B2 | 6/2008 | Gross et al. | |
| 7,396,265 B2 | 7/2008 | Darley et al. | |
| 7,415,308 B2 | 8/2008 | Gerber et al. | |
| 7,444,181 B2 | 10/2008 | Shi et al. | |
| 7,450,991 B2 | 11/2008 | Smith et al. | |
| 7,460,911 B2 | 12/2008 | Cosendai et al. | |
| 7,463,928 B2 | 12/2008 | Lee et al. | |
| 7,470,236 B1 | 12/2008 | Kelleher et al. | |
| 7,483,752 B2 | 1/2009 | VonArx et al. | |
| 7,496,404 B2 | 2/2009 | Meadows et al. | |
| 7,515,967 B2 | 4/2009 | Phillips et al. | |
| 7,532,936 B2 | 5/2009 | Erickson et al. | |
| 7,539,538 B2 | 5/2009 | Parramon et al. | |
| 7,551,960 B2 | 6/2009 | Forsberg et al. | |
| 7,555,346 B1 | 6/2009 | Woods et al. | |
| 7,565,203 B2 | 7/2009 | Greenberg et al. | |
| 7,578,819 B2 | 8/2009 | Bleich et al. | |
| 7,580,752 B2 | 8/2009 | Gerber et al. | |

(56) References Cited

U.S. PATENT DOCUMENTS

| | | | |
|---|---|---|---|
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,659,751 B2 | 2/2010 | Morgenshtein |
| 7,676,275 B1 | 3/2010 | Farazi et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,881,783 B2 | 2/2011 | Bonde et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,019,443 B2 | 9/2011 | Schleicher et al. |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,204,569 B2 | 6/2012 | Gerber et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,802,038 B2 | 10/2017 | Lee et al. |
| 9,907,476 B2 | 3/2018 | Bonde et al. |
| 2002/0147485 A1 | 10/2002 | Mamo |
| 2003/0028231 A1 | 2/2003 | Partridge et al. |
| 2003/0199938 A1 | 10/2003 | Smits et al. |
| 2003/0199962 A1 | 10/2003 | Struble et al. |
| 2004/0054389 A1 | 3/2004 | Osypka |
| 2004/0059401 A1 | 3/2004 | Ollivier et al. |
| 2004/0064158 A1* | 4/2004 | Klein ............... A61N 1/056 607/9 |
| 2004/0087984 A1 | 5/2004 | Kupiecki et al. |
| 2004/0172115 A1 | 9/2004 | Miazga et al. |
| 2004/0230282 A1* | 11/2004 | Cates ............... A61N 1/056 607/126 |
| 2005/0010260 A1 | 1/2005 | Gerber |
| 2005/0096718 A1* | 5/2005 | Gerber ............. A61N 1/0558 607/117 |
| 2005/0102006 A1 | 5/2005 | Whitehurst |
| 2005/0104577 A1 | 5/2005 | Matei et al. |
| 2005/0113877 A1 | 5/2005 | Spinelli et al. |
| 2005/0215946 A1 | 9/2005 | Hansmann |
| 2006/0032657 A1 | 2/2006 | Zarembo |
| 2006/0041295 A1 | 2/2006 | Osypka |
| 2006/0074412 A1 | 4/2006 | Zerfas et al. |
| 2006/0085042 A1 | 4/2006 | Hastings |
| 2006/0095078 A1 | 5/2006 | Tronnes |
| 2006/0206166 A1 | 9/2006 | Weiner |
| 2007/0255368 A1 | 11/2007 | Bonde et al. |
| 2007/0255369 A1 | 11/2007 | Bonde et al. |
| 2007/0265675 A1 | 11/2007 | Lund et al. |
| 2007/0293914 A1 | 12/2007 | Woods et al. |
| 2008/0103570 A1 | 5/2008 | Gerber |
| 2008/0103572 A1 | 5/2008 | Gerber |
| 2008/0161874 A1 | 7/2008 | Bennett et al. |
| 2008/0183236 A1 | 7/2008 | Gerber |
| 2010/0076254 A1 | 3/2010 | Jimenez et al. |
| 2010/0076534 A1 | 3/2010 | Mock |
| 2010/0160997 A1 | 6/2010 | Johnson et al. |
| 2010/0256696 A1 | 10/2010 | Schleicher et al. |
| 2011/0251662 A1 | 10/2011 | Griswold et al. |
| 2011/0270269 A1 | 11/2011 | Swoyer et al. |
| 2011/0282416 A1 | 11/2011 | Hamann et al. |
| 2011/0301667 A1 | 12/2011 | Olson et al. |
| 2011/0313427 A1 | 12/2011 | Gindele et al. |
| 2012/0041512 A1 | 2/2012 | Weiner |
| 2012/0046712 A1 | 2/2012 | Woods et al. |
| 2012/0053665 A1 | 3/2012 | Stolz et al. |
| 2012/0095478 A1 | 4/2012 | Wang et al. |
| 2012/0130448 A1 | 5/2012 | Woods et al. |

(56) References Cited

U.S. PATENT DOCUMENTS

| | | |
|---|---|---|
| 2012/0191169 A1 | 7/2012 | Rothstein et al. |
| 2012/0203320 A1 | 8/2012 | DiGiore et al. |
| 2012/0276854 A1 | 11/2012 | Joshi et al. |
| 2012/0276856 A1 | 11/2012 | Joshi et al. |
| 2012/0310317 A1 | 12/2012 | Lund et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0018447 A1 | 1/2013 | Ollivier et al. |
| 2013/0131766 A1 | 5/2013 | Crosby et al. |
| 2013/0150925 A1 | 6/2013 | Vamos et al. |
| 2013/0150936 A1 | 6/2013 | Takahashi |
| 2013/0150939 A1 | 6/2013 | Burnes et al. |
| 2013/0184773 A1 | 7/2013 | Libbus et al. |
| 2013/0197608 A1 | 8/2013 | Eiger |
| 2013/0207863 A1 | 8/2013 | Joshi |
| 2013/0310894 A1 | 11/2013 | Trier |
| 2013/0331909 A1 | 12/2013 | Gerber |
| 2014/0222112 A1 | 8/2014 | Fell |
| 2014/0237806 A1 | 8/2014 | Smith et al. |
| 2014/0277270 A1 | 9/2014 | Parramon et al. |
| 2015/0214604 A1 | 7/2015 | Zhao et al. |
| 2016/0045724 A1 | 2/2016 | Lee et al. |

FOREIGN PATENT DOCUMENTS

| | | |
|---|---|---|
| EP | 2243509 | 10/2010 |
| WO | WO 1998/20933 | 5/1998 |
| WO | WO 2000/27469 | 5/2000 |
| WO | WO 2000/56677 | 9/2000 |
| WO | WO 2001/60447 | 8/2001 |
| WO | WO 2003/084433 | 10/2003 |
| WO | WO 2006/116205 | 11/2006 |
| WO | WO 2007/022180 | 2/2007 |
| WO | WO 2008/021524 | 2/2008 |
| WO | WO 2008/153726 | 12/2008 |
| WO | WO 2009/102536 | 8/2009 |
| WO | WO 2009/135075 | 11/2009 |
| WO | WO 2010/107751 | 9/2010 |
| WO | WO 2011/059565 | 5/2011 |
| WO | WO 2013/063798 | 5/2013 |
| WO | WO 2013/070490 | 5/2013 |
| WO | WO 2013/156038 | 10/2013 |

OTHER PUBLICATIONS

Examination Report dated Apr. 19, 2010 for European Patent Application 07709826.7 (6 pgs.).
Office Action dated May 16, 2011 for European Application No. 07709826.7, (5 pgs.).
Response to Office Action dated Oct. 29, 2010 for European Application No. 07709826.7, (12 pgs.).
Bosch et al., Sacral (S3) Segmental Nerve Stimulation As A Treatment For Urge Incontinence In Patients With Detrusor Instability: Results Of Chronic Electrical Stimulation Using An Implantable Neural Prosthesis, The Journal of Urology, vol. 154, p. 504-507, Aug. 1995.
Carlton et al., Canine Evaluation of the InterStim® Tined Anchor: Acute Holding Strength, Medtronic Urology, 2002, 4 pages, (Applicant points out, in accordance with MPEP 609.04(a), that the year of publication, 2002, is sufficiently earlier than the effective U.S. filing date, so that the particular month of publication is not in issue.).
Siegel, Management of Voiding Dysfunction With An Implantable Neuroprosthesis, Urologogic Clinics of North America, vol. 19, No. 1, p. 163-170, Feb. 1992.
Medtronic InterStim® Test Stimulation Lead Kit, Technical Manual, 2002, 27 pages, (Applicant points out, in accordance with MPEP 609.04(a), that the year of publication, 2002, is sufficiently earlier than the effective U.S. filing date, so that the particular month of publication is not in issue.).
Medtronic InterStim® Test Stimulation Components, 2002, 41 pages, (Applicant points out, in accordance with MPEP 609.04(a), that the year of publication, 2002, is sufficiently earlier than the effective U.S. filing date, so that the particular month of publication is not in issue.).
Prosecution History from U.S. Appl. No. 11/591,171, dated Apr. 3, 2009 through Sep. 11, 2019 377pp.
Office Action from U.S. Appl. No. 11/591,171, dated Oct. 3, 2019, 14 pp.
Notice of Allowance from U.S. Appl. No. 11/591,171, dated Sep. 11, 2019, 5 pp.

* cited by examiner

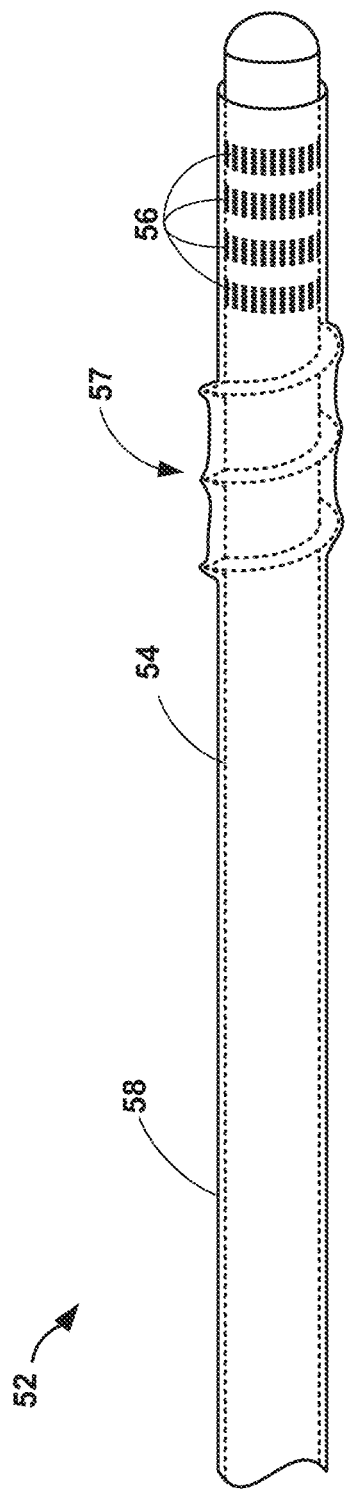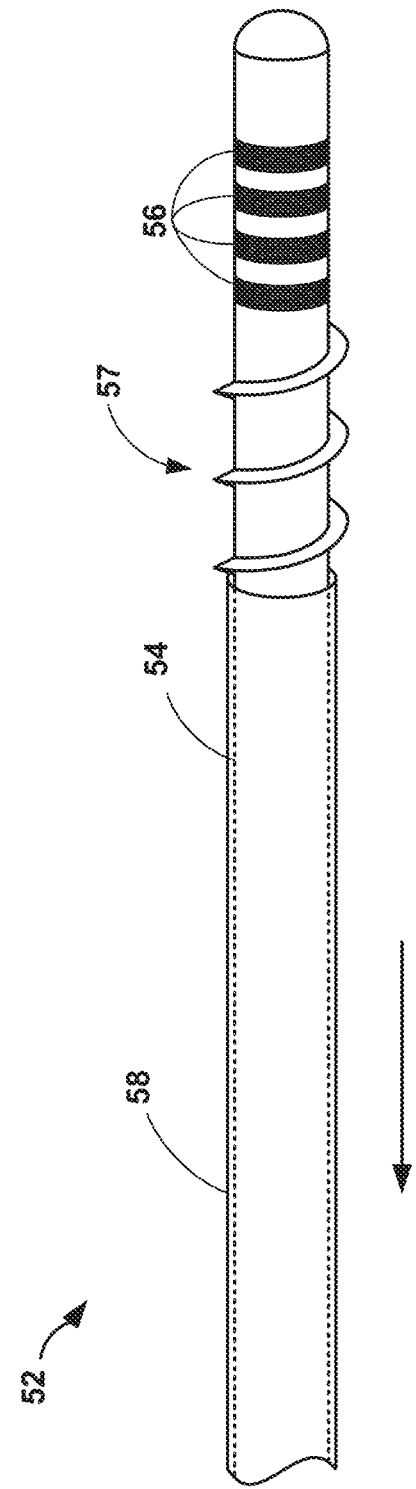
FIG. 3A
FIG. 3B

IMPLANTABLE MEDICAL LEAD WITH THREADED FIXATION

This application is a continuation of U.S. patent application Ser. No. 11/591,171, filed Oct. 31, 2006, the entire contents of which are incorporated herein by reference.

TECHNICAL FIELD

The invention relates to stimulation systems and, more particularly, to stimulation leads in stimulation systems.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, or gastroparesis. An electrical stimulation system typically includes one or more stimulation leads coupled to an external or implantable electrical stimulator. The stimulation lead may be percutaneously or surgically implanted in a patient on a temporary or permanent basis such that at least one stimulation electrode is positioned proximate to a target stimulation site. The target stimulation site may be, for example, a spinal cord, pelvic nerve, pudendal nerve, stomach, muscle, or within a brain or other organ of a patient. The electrodes located proximate to the target stimulation site may deliver stimulation therapy to the target stimulation site in the form of electrical signals.

Electrical stimulation of a sacral nerve may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Thus, in order to deliver electrical stimulation to at least one of the S2, S3, or S4 sacral nerves, a stimulation lead is implanted proximate to the sacral nerve(s).

Electrical stimulation of a peripheral nerve, such as stimulation of an occipital nerve, may be used to induce paresthesia. Occipital nerves, such as a lesser occipital nerve, greater occipital nerve or third occipital nerve, exit the spinal cord at the cervical region, extend upward and towards the sides of the head, and pass through muscle and fascia to the scalp. Pain caused by an occipital nerve, e.g. occipital neuralgia, may be treated by implanting a lead proximate to the occipital nerve to deliver stimulation therapy.

In many stimulation applications, including stimulation of a sacral nerve, it is desirable for a stimulation lead to resist migration following implantation. For example, it may be desirable for the electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between the electrode and a nerve in order to help prevent inflammation to the nerve and in some cases, unintended nerve damage. Securing the stimulation lead at the target stimulation site may minimize lead migration.

SUMMARY

In general, the disclosure is directed toward securing electrodes of a medical lead adjacent to a target tissue site with a threaded fixation structure configured to engage tissue within a patient to resist migration of the medical lead. The medical lead may be similar to a "screw" or "auger-like." The threaded fixation structure defines one or more threads disposed circumferentially about the outer surface of a lead body. Specifically, the threads of the threaded fixation structure may be arranged in a helical pattern. During implantation, a clinician may rotate the entire lead to "screw" the lead into the tissue of the patient until electrodes of the lead reside adjacent to a target tissue. In this manner, the threaded fixation structure secures the lead within the patient to resist lead migration. In addition, the threaded fixation structure may allow a fine adjustment mechanism for the depth of the elongated member within the tissue. The threaded fixation structure may be disposed on a portion of the lead proximal to or distal to the electrodes of the lead or over the portion of the lead that includes the electrodes. In some cases, the entire distal end of the lead may include the threaded fixation structure to engage a greater area of tissue. In other embodiments, the threaded fixation structure may be used with drug delivery catheters instead of electrical stimulation leads.

In one embodiment, the disclosure is directed to a medical lead that includes an elongated member having a proximal end and a distal end, at least one stimulation electrode disposed closer to the distal end of the lead than the proximal end of the lead, and at least one threaded structure extending around a portion of an outer surface of the elongated member and configured to engage tissue within a patient to resist migration of the medical lead.

In another embodiment, the disclosure is directed to method that includes inserting a medical lead into a patient, wherein the lead comprises at least one stimulation electrode and at least one threaded fixation structure extending around a portion of an outer surface of the lead, and rotating the lead to engage the threaded fixation structure with tissue of the patient to resist migration of the lead.

In an additional embodiment, the disclosure is directed to a system that includes a medical lead having an elongated member having a proximal end and a distal end, at least one stimulation electrode disposed closer to the distal end of the lead than the proximal end of the lead, and at least one threaded structure extending around a portion of an outer surface of the elongated member and configured to engage tissue within a patient to resist migration of the medical lead. The system also includes a stimulator that delivers electrical stimulation therapy to a patient via the medical lead within the patient.

In another additional embodiment, the disclosure is directed to an apparatus that includes an elongated member having a proximal end and a distal end, a conduit disposed within the elongated member, an exit port disposed on an outer surface of the elongated member in fluidic communication with the conduit, and at least one threaded fixation structure extending around a portion of an outer surface of the elongated member and configured to engage tissue within a patient to resist migration of the medical lead.

The disclosure may provide one or more advantages. The threaded fixation structure may be engaged to the adjacent tissue of the patient and still allow the clinician to advance or retract the lead to finely adjust the lead position. A sheath may also be used to cover the threaded fixation structure until the clinician desires to expose the threaded fixation structure to the adjacent tissue, and the sheath may collapse the threaded fixation structure to reduce the lead diameter until lead fixation is desired. In addition, the clinician may remove the lead by rotating the lead and reducing tissue trauma.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A and 3B are perspective drawings of a sheath that covers a lead prior to implantation and is removed after the lead is correctly positioned in a patient.

DETAILED DESCRIPTION

The medical leads described herein include a threaded fixation mechanism that secures the medical lead within a tissue of a patient. The threaded fixation mechanism prevents the electrodes of the lead from migrating away from the target stimulation tissue, which may lead to a reduction in therapy efficacy. Specifically, the threaded fixation mechanism includes a thread structure disposed around the outer surface of the elongated member, such that the lead resembles a "screw" or "auger" device that advances or retreats when rotated. The threaded fixation mechanism may allow the clinician to finely adjust the elongated member location, in contrast to other medical lead fixation structures such as tines or adhesives. Generally, the threads may be arranged in a helical pattern, but other types of thread patterns may also be used to secure the lead. Hence, the threaded fixation mechanism may be referred to as a threaded fixation structure for purposes of illustration. In addition, other non-helical thread patterns may be used in some embodiments. The thread structure may be disposed distal to the electrodes, proximal to the electrodes, and/or at the same axial position of the electrodes. In addition, in some embodiments, the threaded fixation structure may be disposed on a tapered tip at the distal end of the elongated member to begin the engagement and tunneling of the lead through the tissue when the lead is rotated to secure the threaded fixation structure.

In some embodiments, the thread structure may not engage the adjacent tissue until the user, e.g. a clinician, desires the structure to do so. For example, a sheath may be configured to cover the elongated member and thread structure for lead insertion and be removed to allow the threaded fixation structure to contact the adjacent tissue. In addition, the thread structure may fold down against the elongated member outer surface when constricted by the sheath. When the clinician removes the sheath, the threaded fixation structure extends away from the elongated member and returns to its original thread shape to secure the lead. In this case, the thread structure may have elastic, super-elastic, or shape memory properties that cause it to assume an extended position when a sheath or other restraint mechanism is removed to expose the thread structure.

Alternatively, the medical lead may not include electrodes on the elongated member. In this case, the medical lead may be a catheter that delivers a therapeutic agent through one or more lumens in the elongated member, while the threaded fixation structure secures the location of the catheter. The lumen may end at one or more exit ports near the distal end of the elongated member, and the exit ports may be disposed in an axial or longitudinal outer surface of the elongated member.

Figure 1A:
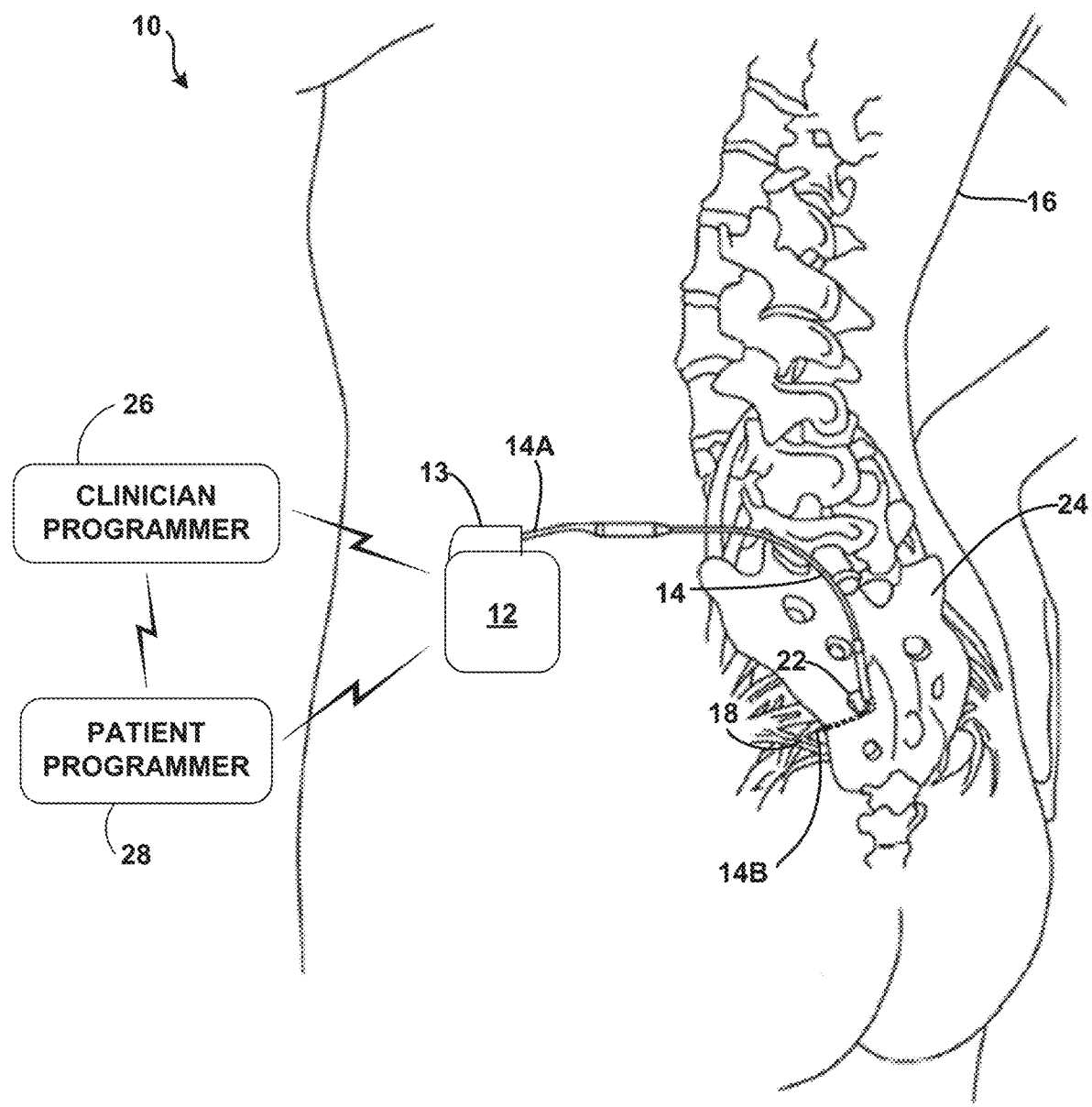
FIG. 1A is a schematic perspective view of a therapy system including an electrical stimulator coupled to a stimulation lead that has been implanted in a body of a patient proximate to a target stimulation site.

FIG. 1A a schematic perspective view of therapy system 10, which includes electrical stimulator 12 coupled to stimulation lead 14, which has been implanted in body 16 of a patient proximate to target stimulation site 18. Electrical stimulator 12 provides a programmable stimulation signal (e.g., in the form of electrical pulses or substantially continuous-time signals) that is delivered to target stimulation site 18 by stimulation lead 14, and more particularly, via one or more stimulation electrodes carried by lead 14. Electrical stimulator 12 may be either implantable or external. For example, electrical stimulator 12 may be subcutaneously implanted in the body of a patient 16 (e.g., in a chest cavity, lower back, lower abdomen, or buttocks of patient 16). Electrical stimulator 12 may also be referred to as a pulse or signal generator, and in the embodiment shown in FIG. 1A, electrical stimulator 12 may also be referred to as a neurostimulator. In some embodiments, lead 14 may also carry one or more sense electrodes to permit stimulator 12 to sense electrical signals from target stimulation site 18. Furthermore, in some embodiments, stimulator 12 may be coupled to two or more leads, e.g., for bilateral or multi-lateral stimulation.

Lead 14 further includes a lead body, or elongated member, and one or more threaded fixation structures (not shown in FIG. 1) which engage with tissue proximate to target stimulation site 18 to substantially fix a position of lead 14 proximate to target stimulation site 18. The threaded fixation structure is rotated during implantation to engage with tissue adjacent to target stimulation site 18. Proximal end 14A of lead 14 may be both electrically and mechanically coupled to connector 13 of stimulator 12 either directly or via a lead extension. In particular, lead 14 may include electrical contacts near proximal end 14A to electrically connect conductors disposed within the elongated member to stimulation electrodes (and sense electrodes, if present) at a position adjacent to distal end 14B of lead 14 to stimulator 12. Lead 14 may be connected directly or indirectly (e.g., via a lead extension) to stimulator 12.

In the example embodiment of therapy system 10 shown in FIG. 1A, target stimulation site 18 is proximate to the S3 sacral nerve, and lead 14 has been introduced into the S3 sacral foramen 22 of sacrum 24 to access the S3 sacral nerve. Stimulation of the S3 sacral nerve may help treat pelvic floor disorders, urinary control disorders, fecal control disorders, interstitial cystitis, sexual dysfunction, and pelvic pain. Therapy system 10, however, is useful in other stimulation applications. Thus, in alternate embodiments, target stimulation site 18 may be a location proximate to any of the other sacral nerves in body 16 or any other suitable nerve in body 16, which may be selected based on, for example, a therapy program selected for a particular patient. For example, in other embodiments, therapy system 10 may be used to deliver stimulation therapy to pudendal nerves, perineal nerves, or other areas of the nervous system, in which cases, lead 14 would be implanted and substantially fixed proximate to the respective nerve. As further alternatives, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although sacral nerve stimulation will be described herein for purposes of illustration, a stimulation lead 14 in accordance with the invention may be adapted for application to a variety of electrical stimulation applications.

Migration of lead 14 following implantation may be undesirable, and may have detrimental effects on the quality of therapy delivered to a patient 16. For example, migration of lead 10 may cause displacement of electrodes carried by lead 14 to a target stimulation site 18. As a result, the electrodes may not be properly positioned to deliver the therapy, possibly undermining therapeutic efficacy of the stimulation therapy from system 10. Substantially fixing lead 14 to surrounding tissue may help discourage lead 14 from migrating from target stimulation site 18 following implantation, which may ultimately help avoid harmful effects that may result from a migrating stimulation lead 14.

To that end, the invention provides lead 14 with a thread structure (not shown in FIG. 1) disposed around the elongated member of lead 14 to provide fixation between lead 14 and tissue surrounding lead 14, such as tissue within sacrum 16 in the example of FIG. 1A. The thread structure may have a helical pattern that permits lead 14 to be, in effect, screwed into a tissue site. In comparison to some existing methods of fixing implanted medical leads, such as suturing lead 14 to surrounding tissue or applying a cuff electrode, using a threaded fixation structure to secure lead 14 in patient 16 may be beneficial in a minimally invasive surgery, which may allow for reduced pain and discomfort for patient 16 relative to invasive surgery, as well as a quicker recovery time. As described in further detail below, the threaded fixation structure is disposed around the outer surface of the elongated body near the distal end of lead 14 and configured to engage with the adjacent tissue to prevent lead 14 movement.

Implanting lead 14 with the threaded fixation structure may be completed via a few methods. First, the clinician may rotate lead 14 to advance lead 14 toward target stimulation sire 18 and utilize the threaded fixation structure to engage the adjacent tissue. Second, a sheath (not shown in FIG. 1A) may be used initially to cover lead 14 and the included threaded fixation structure to allow the clinician to insert lead 14 into patient 16 until direct insertion is no longer possible. At this point, the clinician may remove the sheath to expose the threaded fixation structure and then rotate lead 14 to advance lead 14 the rest of the distance towards target stimulation site 18.

The rotation of lead 14 may be achieved directly by rotating the lead body, or by a stylet or other device that is inserted into an inner lumen of the lead to engage the lead. In some embodiments, the stylet may have a keyed structure, such as one or more longitudinal flanges, ribs, teeth or grooves that engage reciprocal structure in the inner lumen of the lead. For example, a keyed stylet may be inserted to engage the distal end of the lead and lock into interior grooves or teeth to facilitate the rotation of the lead. In particular, reciprocal teeth or grooves, or the like, may rotationally bear against each other such that rotation of the stylet causes rotation of the lead in the same direction.

In addition, the threaded fixation structure may be foldable against the elongated member of lead 14 when covered by the sheath. When the sheath is removed, the threaded fixation structure may stand up, or extend, away from the elongated member to its original shape. The clinician may then rotate lead 14 to advance lead 14 to target stimulation site 18. In either case, the thread tends to "bite" into the surrounding tissue to resist migration of the lead from the target stimulation site.

Therapy system 10 also may include a clinician programmer 26 and a patient programmer 28. Clinician programmer 26 may be a handheld computing device that permits a clinician to program stimulation therapy for patient 16, e.g., using input keys and a display. For example, using clinician programmer 26, the clinician may specify stimulation parameters for use in delivery of stimulation therapy. Clinician programmer 26 supports telemetry (e.g., radio frequency telemetry) with stimulator 12 to download stimulation parameters and, optionally, upload operational or physiological data stored by stimulator 12. In this manner, the clinician may periodically interrogate stimulator 12 to evaluate efficacy and, if necessary, modifies the stimulation parameters.

Like clinician programmer 26, patient programmer 28 may be a handheld computing device. Patient programmer 28 may also include a display and input keys to allow patient 16 to interact with patient programmer 28 and implantable stimulator 12. In this manner, patient programmer 28 provides patient 16 with an interface for control of stimulation therapy by stimulator 12. For example, patient 16 may use patient programmer 28 to start, stop or adjust stimulation therapy. In particular, patient programmer 28 may permit patient 16 to adjust stimulation parameters such as duration, amplitude, pulse width and pulse rate, within an adjustment range specified by the clinician via clinician programmer 28, or select from a library of stored stimulation therapy programs.

Figure 2:
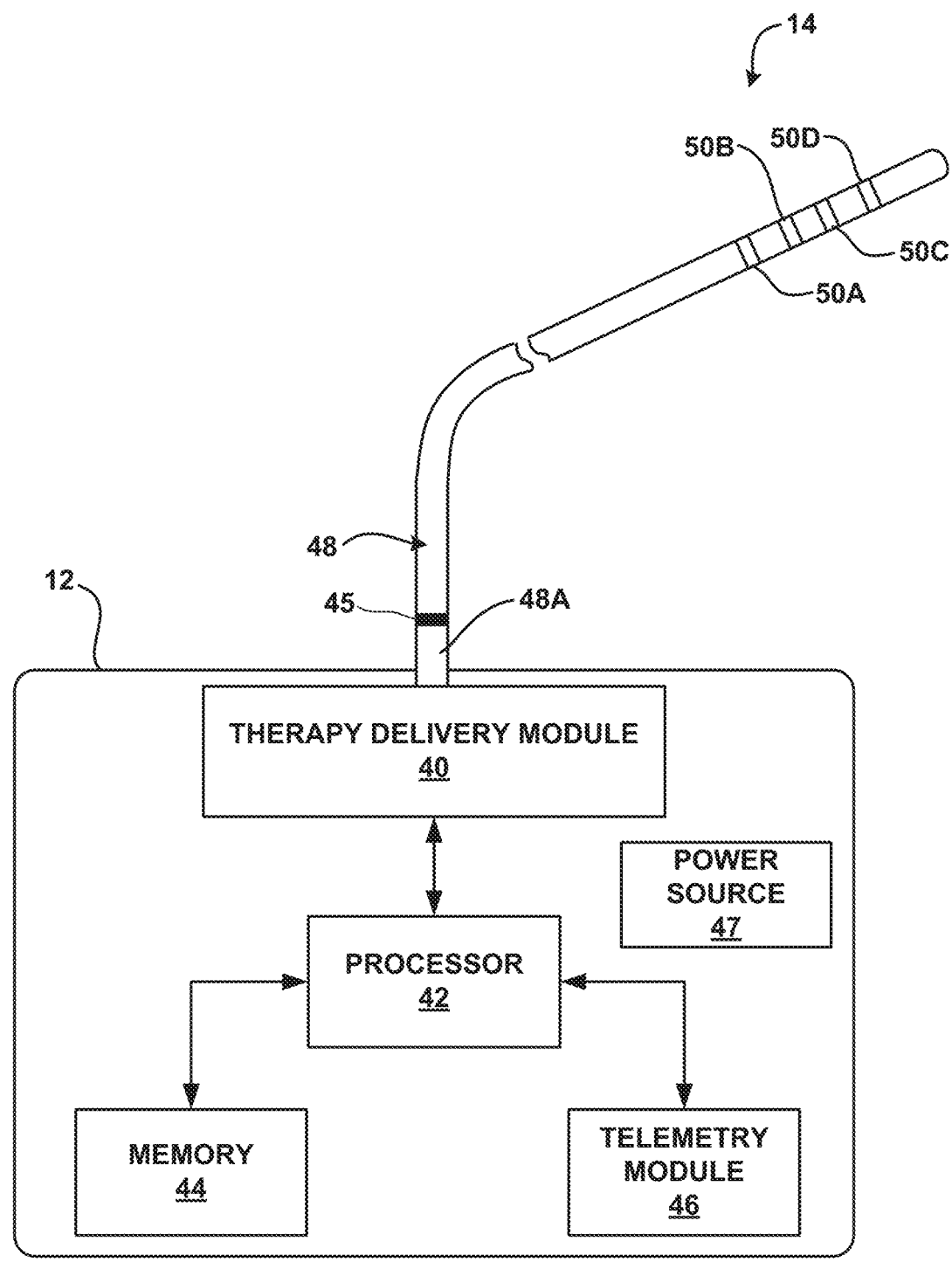
FIG. 2 is a block diagram illustrating various components of an electrical stimulator and an implantable lead.

Stimulator 12, clinician programmer 26, and patient programmer 28 may communicate via cables or a wireless communication, as shown in FIG. 2. Clinician programmer 26 and patient programmer 28 may, for example, communicate via wireless communication with stimulator 12 using radio frequency (RF) telemetry techniques known in the art. Clinician programmer 26 and patient programmer 28 also may communicate with each other using any of a variety of local wireless communication techniques, such as RF communication according to the 802.11 or Bluetooth specification sets, or other standard or proprietary telemetry protocols.

Figure 1B:
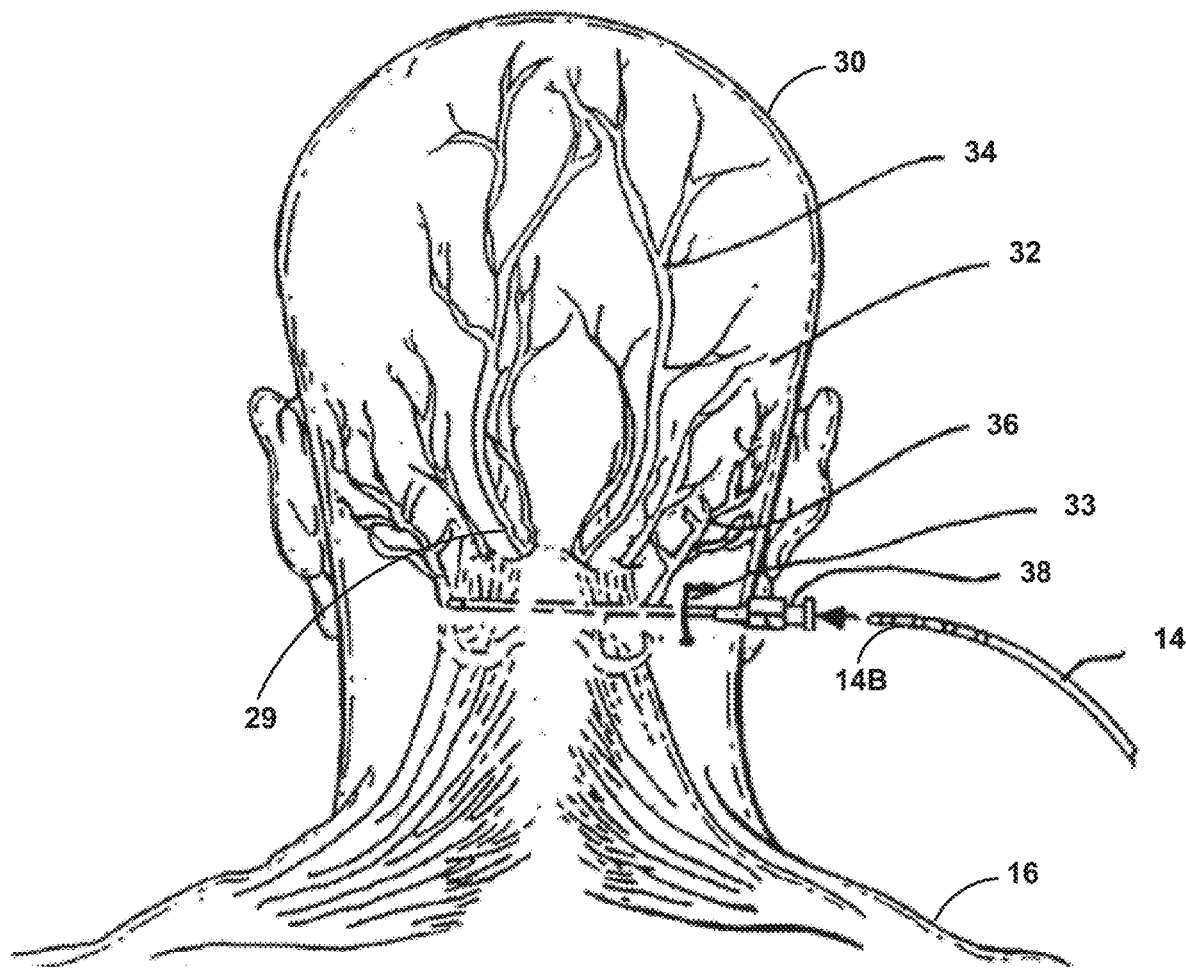
FIG. 1B is an illustration of the implantation of a stimulation lead at a location proximate to an occipital nerve.

FIG. 1B is a conceptual illustration of an alternative implantation site to the implantation of FIG. 1A. Therapy system 10 may also be used to provide stimulation therapy to other nerves of a patient 16. For example, as shown in FIG. 1B, lead 14 may be implanted and fixated with the two or more threaded fixation members proximate to an occipital region 29 of patient 30 for stimulation of one or more occipital nerves. In particular, lead 14 may be implanted proximate to lesser occipital nerve 32, greater occipital nerve 34, and third occipital nerve 36. In FIG. 1B, lead 14 is aligned to be introduced into introducer needle 38 and implanted and anchored or fixated with fixation elements proximate to occipital region 29 of patient 30 for stimulation of one or more occipital nerves 32, 34, and/or 36. A stimulator (e.g., stimulator 12 in FIG. 1A) may deliver stimulation therapy to any one or more of occipital nerve 32, greater occipital nerve 34 or third occipital nerve 36 via electrodes disposed adjacent to distal end 14B of lead 14. In alternate embodiments, lead 14 may be positioned proximate to one or more other peripheral nerves proximate to occipital nerves 32, 34, and 36 of patient 30, such as nerves branching from occipital nerves 32, 34, and 36, as well as stimulation of any other suitable nerve, organ, muscle, muscle group or other tissue site within patient 30, such as, but not limited to, nerves within a brain, pelvis, stomach or spinal cord of patient 30.

Implantation of lead 14 may involve the subcutaneous placement of lead 14 transversely across one or more occipital nerves 32, 34, and/or 36 that are causing patient 30 to experience pain. In one example method of implanting lead 14 proximate to the occipital nerve, using local anesthesia, a vertical skin incision 33 approximately two centimeters in length is made in the neck of patient 30 lateral to the midline of the spine at the level of the C1 vertebra. The length of vertical skin incision 33 may vary depending on the particular patient. At this location, patient's skin and muscle are separated by a band of connective tissue referred to as fascia. Introducer needle 38 is introduced into the subcutaneous tissue, superficial to the fascia and muscle layer but below the skin. Occipital nerves 32, 34, and 36 are located within the cervical musculature and overlying fascia, and as a result, introducer needle 38 and, eventually, lead 14 are inserted superior to occipital nerves 32, 34, and 36.

Once introducer needle 38 is fully inserted, lead 14 may be advanced through introducer needle 38 and positioned to allow stimulation of the lesser occipital nerve 32, greater occipital nerve 34, third occipital nerve 36, and/or other peripheral nerves proximate to an occipital nerve. Upon placement of lead 14, introducer needle 38 may be removed. In some embodiments, introducer needle 38 may be used to remove lead 14 after stimulation therapy is no longer needed.

Accurate lead placement may affect the success of occipital nerve stimulation. If lead 14 is located too deep, i.e., anterior, in the subcutaneous tissue, patient 30 may experience muscle contractions, grabbing sensations, or burning. Such problems may additionally occur if lead 14 migrates after implantation. Furthermore, due to the location of implanted lead 14 on the back of patient's 30 neck, lead 14 may be subjected to pulling and stretching that may increase the chances of lead migration. For these reasons, lead 14 may employ the threaded fixation structure to secure lead 14 within patient 16. In locations near the skin of patient 16, the threaded fixation structure may only extend from the elongated body of lead 14 a small distance to minimize patient detection of the threaded fixation structure at superficial implant locations. In other words, the thread structure may be sized so as not to protrude excessively into the superficial tissues, thereby avoiding skin deformations and potential tissue erosion and damage.

Although lead 14 has been generally described as an electrical lead that includes electrodes, lead 14 may, in other embodiments, be a drug delivery catheter that delivers therapeutic agents to target stimulation site 18 (FIG. 1A) or occipital nerves 32, 34 or 36. In this case, stimulator 12 is a drug pump that controls the delivery of therapeutic agent to patient 16. The drug delivery catheter embodiment of lead 14 may include an exit port for the therapeutic agent that is disposed on any surface of lead 14, adjacent to or within the threaded fixation structure.

FIG. 2 is a block diagram illustrating various components of implantable stimulator 12 and an implantable lead 14. Stimulator 12 includes therapy delivery module 40, processor 42, memory 44, telemetry module 46, and power source 47. In some embodiments, stimulator 12 may also include a sensing circuit (not shown in FIG. 2). Implantable lead 14 includes elongated member 48 extending between proximal end 48A and distal end 48B. Elongated member 48 may also be described as an elongated member. Elongated member 48 may be a cylindrical or may be a paddle-shaped (i.e., a "paddle" lead). Electrodes 50A, 50B, 50C, and 50D (collectively "electrodes 50") are disposed on elongated member 48 adjacent to distal end 48B of elongated member 48. In the example of FIG. 2, threaded fixation structures are omitted from lead 14 for ease of illustration.

Stimulator 12 delivers stimulation therapy via electrodes 50 of lead 14. In particular, implantable signal generator within therapy delivery module 40 delivers electrical signals to patient 16 (FIG. 1A) via at least some of electrodes 50 under the control of a processor 42. The stimulation energy generated by therapy delivery module 40 may be formulated as stimulation energy, e.g., for treatment of any of a variety of neurological disorders, or disorders influenced by patient neurological response. The signals may be delivered from therapy delivery module 40 to electrodes 50 via a switch matrix and conductors carried by lead 14 and coupled to respective electrodes 50.

In some embodiments, electrodes 50 may be ring electrodes. In other embodiments, electrodes 50 may be segmented or partial ring electrodes, each of which extends along an arc less than 360 degrees (e.g., 90-120 degrees) around the circumference of elongated member 48. In embodiments in which lead 14 is a paddle lead, electrodes 50 may extend along a portion of the periphery defined by elongated member 48. Electrodes 50 are electrically coupled to a therapy delivery module 40 of stimulator 12 via conductors within elongated member 48.

Electrodes 50 extending around a portion of the circumference of lead body 48 or along one side of a paddle lead may be useful for providing an electrical stimulation field in a particular direction/targeting a particular therapy delivery site. For example, in the electrical stimulation application shown in FIG. 1B, electrodes 50 may be disposed along lead body 48 such that the electrodes face toward occipital nerves 32, 34, and/or 36, or otherwise away from the scalp of patient 30. This may be an efficient use of stimulation because electrical stimulation of the scalp may provide minimally useful therapy, if any, to patient 30. In addition, the use of segmented or partial ring electrodes 50 may also reduce the overall power delivered to electrodes 50 by stimulator 12 because of the efficient delivery of stimulation to occipital nerves 32, 34, and/or 36 (or other target stimulation site) by eliminating or minimizing the delivery of stimulation to unwanted or unnecessary regions within patient 30. The configuration, type, and number of electrodes 28 illustrated in FIG. 2 are merely exemplary.

In embodiments in which electrodes 50 extend around a portion of the circumference of lead body 48 or along one side of a paddle lead, lead 14 may include one or more orientation markers 45 proximate to proximal end 14A that indicate the relative location of electrodes 50. Orientation marker 45 may be a printed marking on lead body 48, an indentation in lead body 48, a radiographic marker, or another type of marker that is visible or otherwise detectable (e.g., detectable by a radiographic device) by a clinician. Orientation marker 45 may help a clinician properly orient lead 14 such that electrodes 50 face the desired direction (e.g., toward occipital nerves 32, 34, and/or 36) within patient 16. For example, orientation marker 45 may also extend around the same portion of the circumference of lead body 48 or along the side of the paddle lead as electrodes 50. In this way, orientation marker 45 faces the same direction as electrodes, thus indicating the orientation of electrodes 50 to the clinician. When the clinician implants lead 14 in patient 16, orientation marker 45 may remain visible to the clinician.

Stimulator 12 delivers stimulation therapy via electrodes 50 of lead 14. In one embodiment, an implantable signal generator or other stimulation circuitry within therapy delivery module 40 delivers electrical signals (e.g., pulses or substantially continuous-time signals, such as sinusoidal signals) to targets stimulation site 18 (FIG. 1A) via at least some of electrodes 50 under the control of a processor 42. The stimulation energy generated by therapy delivery module 40 may be formulated as stimulation energy, e.g., for treatment of any of a variety of neurological disorders, or disorders influenced by patient neurological response. The signals may be delivered from therapy delivery module 40 to electrodes 50 via a switch matrix and conductors carried by lead 14 and electrically coupled to respective electrodes 50. The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

Processor 42 may include a microprocessor, a controller, a DSP, an ASIC, an FPGA, discrete logic circuitry, or the like. Processor 42 controls the implantable signal generator within therapy delivery module 40 to deliver stimulation therapy according to selected stimulation parameters. Specifically, processor 42 controls therapy delivery module 40 to deliver electrical signals with selected amplitudes, pulse widths (if applicable), and rates specified by the programs. In addition, processor 42 may also control therapy delivery module 40 to deliver the stimulation signals via selected subsets of electrodes 50 with selected polarities. For example, electrodes 50 may be combined in various bipolar or multi-polar combinations to deliver stimulation energy to selected sites, such as nerve sites adjacent the spinal column, pelvic floor nerve sites, or cranial nerve sites.

In addition, processor 42 may control therapy delivery module 40 to deliver each signal according to a different program, thereby interleaving programs to simultaneously treat different symptoms or provide a combined therapeutic effect. For example, in addition to treatment of one symptom such as sexual dysfunction, stimulator 12 may be configured to deliver stimulation therapy to treat other symptoms such as pain or incontinence.

Memory 44 of stimulator 12 may include any volatile or non-volatile media, such as a RAM, ROM, CD-ROM, NVRAM, EEPROM, flash memory, and the like. In some embodiments, memory 44 of stimulator 12 may store multiple sets of stimulation parameters that are available to be selected by patient 16 or a clinician for delivery of stimulation therapy. For example, memory 44 may store stimulation parameters transmitted by clinician programmer 26 (FIG. 1A). Memory 44 also stores program instructions that, when executed by processor 42, cause stimulator 12 to deliver stimulation therapy. Accordingly, computer-readable media storing instructions may be provided to cause processor 42 to provide functionality as described herein.

In particular, processor 42 controls telemetry module 170 to exchange information with an external programmer, such as clinician programmer 26 and/or patient programmer 28 (FIG. 1A), by wireless telemetry. In addition, in some embodiments, telemetry module 46 supports wireless communication with one or more wireless sensors that sense physiological signals and transmit the signals to stimulator 12.

In some embodiments, where lead 14 is a drug delivery catheter, therapy delivery module 40 may include a fluid pump or other release mechanism to dispense a therapeutic agent through lead 14 and into patient 16. Therapy deliver module 40 may also, in this case, include a fluid reservoir which contains the therapeutic agent. Possible therapeutic agents may include pharmaceutical agents, insulin, a pain relieving agent or a gene therapy agent. Refilling the fluid reservoir may be accomplished by inserting the needle of a syringe through the skin of patient 16 and into a refill port in the housing of stimulator 12. In addition, more than one lead may be coupled to therapy delivery module 40.

FIGS. 3A and 3B are perspective drawings of a sheath that covers a lead prior to implantation and removed after the lead is correctly positioned in a patient, which includes a lead that includes a threaded fixation structure. As shown in FIG. 3A, lead 52 is capable of delivering electrical stimulation to numerous tissue sites within patient 16. Lead 52 may be an embodiment of any lead described herein, including lead 14. Prior to delivering stimulation, elongated member 54 of lead 52 is covered completely around the longitudinal outer surface with sheath 58. Sheath 58 may be constructed to protect electrodes 56 and threaded fixation structure 57 from implantation stresses or damage of adjacent tissues. In addition, sheath 58 may be a restraint mechanism that keeps threaded fixation structure 57 from being deployed until the clinician removed the sheath. Electrodes 56 are typically ring electrodes, but other types of electrodes may be used. For example, segmented electrodes, or multiple electrodes around the circumference of elongated member 54 may be employed. Alternatively, lead 52 may be in a non-circular shape, such as a rectangular paddle lead. In some embodiments, lead 52 may also include one or more radio-opaque markers that allow the clinician to image the lead in real time to determine the exact position of the lead within patient after rotating the lead.

Sheath 58 may be constructed of a flexible polymer that provides a smooth interface between the sheath and elongated member 54. Sheath 58 may be dimensioned just larger than elongated member 54, or the sheath may be shrunk to fit elongated member 54 snugly for implantation. In some embodiments, sheath 58 may constructed to assist the clinician in guiding lead 52 within patient 16. In this case, sheath 58 may be rigid or semi-rigid and similar to a lead introducer or a cannula introduction device.

FIG. 3B shows lead 52 with sheath 58 being removed from elongated member 54 in the direction of the arrow. Once lead 52 is positioned such that electrodes 56 are adjacent to a target tissue for stimulation, the clinician may begin removing lead 52 as shown. As sheath 58 is removed, threaded fixation structure 57 is exposed to the adjacent tissue to fix elongated member 54 in position. In other embodiments, the clinician may remove sheath 58 in sections as fixation elements need to be deployed or as necessary to ensure proper fixation within patient 16. As will be described in detail below, threaded fixation structure 57 may have different dimensions, sizes, locations, and properties than shown in FIGS. 3A and 3B.

Figure 4A:
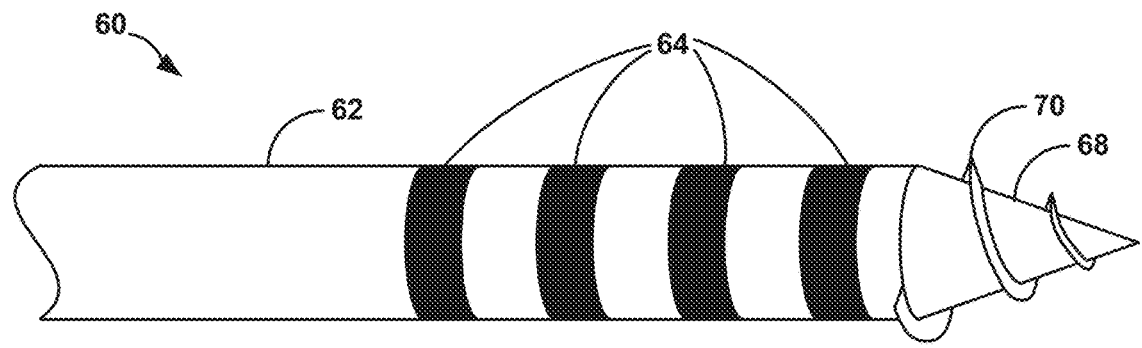
FIGS. 4A-4C are perspective drawings illustrating exemplary stimulation leads with varying configurations of threaded fixation mechanisms.
Figure 4B:
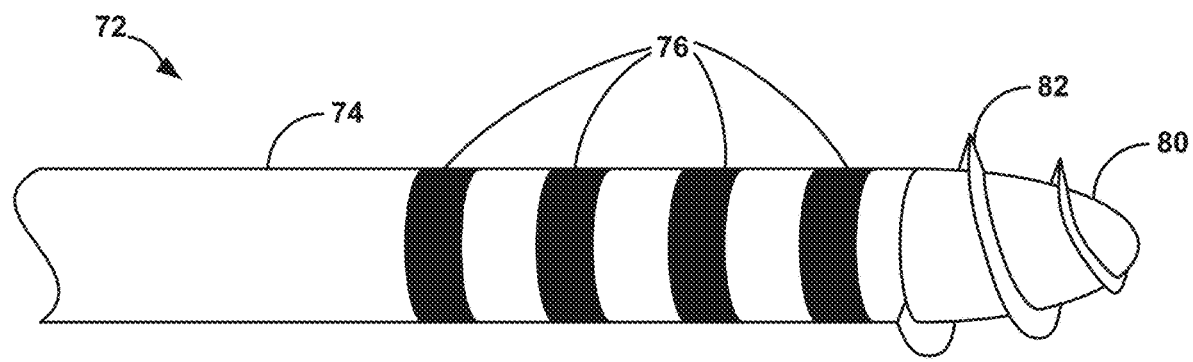
Figure 4C:
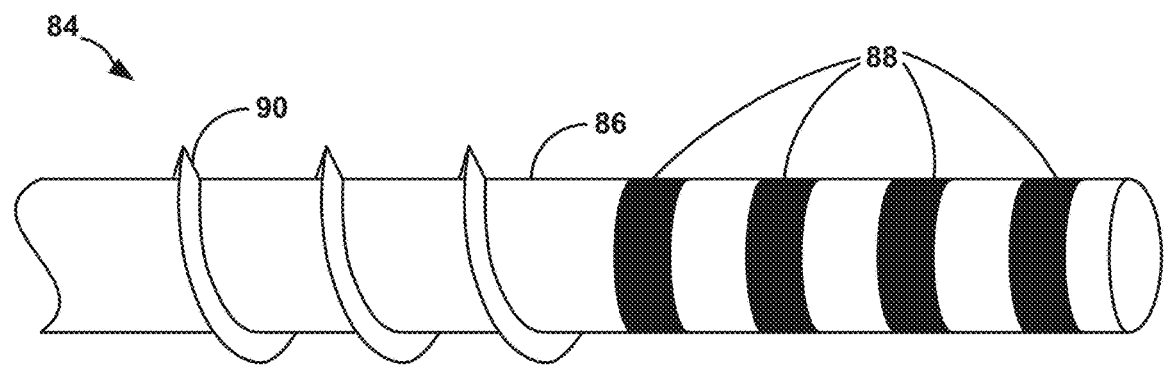

FIGS. 4A-4C are perspective drawings illustrating exemplary stimulation leads with varying configurations of threaded fixation mechanisms. As shown in FIG. 4A, lead 60 includes elongated member 62, electrodes 64, tapered tip 68, and threaded fixation structure 70. The distal end of lead 60 is shown. Elongated member 62 is substantially cylindrical in shape, but the elongated member may also be configured into any other shape. Electrodes 64 are ring electrodes disposed at the distal end of elongated member 62. At the distal tip of lead 60, tapered, conical tip 68 is attached to, or integrally formed with, elongated member 62. Threaded fixation structure 70 is disposed distal to electrodes 64 and around the outer surface of tapered tip 68.

Tapered tip 68 is formed in the shape of a cone to facilitate the tunneling of lead 60 through tissue in order to reach the target tissue. Threaded fixation structure 70 is disposed around the outer surface of tapered tip 68 from adjacent to the distal end of the tapered tip to the distal end of elongated member 62. In this manner, threaded fixation structure 70 engages with the adjacent tissue of patient 16 as tapered tip 68 pierces through the tissue. As a user, e.g., a clinician, rotates lead 60, threaded fixation structure 70 advances the lead through the adjacent tissue and moves electrodes 64 increasingly closer to a target tissue with each turn of the lead. In other embodiments threaded fixation structure 70 may only be disposed along a portion of tapered tip 68.

Threaded fixation structure 70 may be constructed of a material similar to or different from elongated member 62 or tapered tip 68. The material of threaded fixation structure 70 may be substantially biologically inert, e.g., biocompatible, and may include any of metals, metal alloys, composites, or polymers. Some example materials may include stainless steel, titanium, nitinol, polypropylene, polyurethane, polycarbonate, polyethylene, nylon, silicone rubber, or expanded-polytetrafluoroethylene. The material selection of threaded fixation structure 70 may be based upon whether the structure is desired to be rigid, semi-rigid, or flexible properties, which could affect the engagement of the structure to the adjacent material. In addition, threaded fixation structure 70 may be a combination of different materials depending on the implantation site. For example, threaded fixation structure 70 may have a flexible distal portion that changes to a rigid portion for precise engagement with the adjacent tissue. Threaded fixation structure 70 may be adhered to tapered tip 68 through a glue, an epoxy, welding, soldering, or any other attachment mechanism. In other embodiments, threaded fixation structure 70 may be an overmold that is fitted to a snug fit around elongated member 62. Alternatively, threaded fixation structure 70 may be formed with tapered tip 68.

In addition, threaded fixation structure 70 may have a cross-sectional shape configured to assist the advancement of lead 60 through the adjacent tissue. The cross-sectional shape of each thread may generally be a triangle, but other shapes are possible. For example, the cross-sectional shape of threaded fixation structure 70 may be a rounded triangle, a semi-circle, a square, a rectangle, a trapezoid, or any other shape desired by the clinician. In addition, the cross-sectional shape may be angled in a direction non-perpendicular to the outer surface of tapered tip 68. For example, threaded fixation structure 70 may be tilted toward the proximal end of lead 60. In other words, the angle between the outer surface of tapered tip 68 and the proximal side of threaded fixation structure 70 may be less than 90 degrees. Alternatively, the angle between the outer surface of tapered tip 68 and the proximal side of threaded fixation structure 70 may be greater than 90 degrees.

Threaded fixation structure 70 may also be configured to advance through tissue at a predetermined rate or extend into the tissue a predetermined distance. The pitch of threaded fixation structure 70 may be defined by the distance lead 60 is advanced with each full 360 degree rotation of the lead, i.e., the axial distance between two peaks of the threaded fixation structure. Threaded fixation structure 70 may have a pitch between approximately 0.5 millimeters (mm) and 3 mm. The pitch may be less than approximately 0.5 mm or greater than 3 mm. The height of threaded fixation structure 70 is the distance between the outer surface of tapered tip 68 and the top edge of the threaded fixation structure. Generally, the height is between approximately 0.1 mm and 3 mm. However, other embodiments of threaded fixation structure 70 may include heights smaller than approximately 0.1 mm or greater than 3 mm. While threaded fixation structure 70 may have a constant height, the threaded fixation structure may increase in height as the threaded fixation structure moves away from the distal end of tapered tip 68. Generally, elongated member 62 may have an outside diameter between approximately 0.5 mm and 5 mm. The wall thickness of elongated member 62 may be between approximately 0.1 mm and 2 mm. In addition, the ratio of diameter to thread height may be between approximately 1 and 50, depending on the application of lead 60.

FIG. 4B shows lead 72, which is an embodiment of lead 60 (FIG. 4A). Lead 72 includes elongated member 74, electrodes 76, tapered tip 80, and threaded fixation structure 82. Lead 72 differs from lead 60 in the shape of tapered tip 80. While tapered tip 68 is constructed as a cone shape, tapered tip 80 is a parabolic shape with an atraumatic, rounded distal end. Tapered tip 80 may be beneficial if the clinician does not want a tip that may damage adjacent tissue during extreme bends of elongated member 74. In other embodiments, tapered tip 80 may be configured into a different shape. For example, tapered tip 80 may be curved in any parabolic shape different from that shape of the tapered tip shown in FIG. 4B. In addition, tapered tip 80 may be asymmetrical or bent in a predetermined direction to facilitate creating a curved path for lead 72.

FIG. 4C illustrates lead 84 with threaded fixation structure 90 disposed proximal to electrodes 88. Lead 84 includes elongated member 86, electrodes 88 and threaded fixation structure 90. Threaded fixation structure 90 is disposed around the longitudinal outer surface of elongated member 86, proximal to the location of electrodes 88. In other embodiments, threaded fixation structure 90 may be disposed around the longitudinal outer surface of elongated member 86 at a location distal to electrodes 88. The distal position of threaded fixation structure 90 may be instead of or in addition to the proximal position of the threaded fixation structure.

Threaded fixation structure 90 may include any number of turns around elongated member 86. For example, threaded fixation structure 90 may include 3 complete turns as shown in FIG. 4C. However, threaded fixation structure 90 may include more than 3 or less than 3 turns, as desired by the clinician for a particular implantation site. In addition, threaded fixation structure 90 may include partial turns, or even continuous structures with less than one complete turn. In other embodiments, multiple threaded fixation structures 90 may be disposed proximal to or distal to electrodes 88. In alternative embodiments, lead 84 may include a tip that has a threaded fixation structure such as tapered tips 68 and 80 of leads 60 and 72, respectively.

Threaded fixation structure 90 may be constructed of a material similar to or different from elongated member 86. The material of threaded fixation structure 90 may be substantially biologically inert, e.g., biocompatible, and may include any of metals, metal alloys, composites, or polymers. Some example materials may include stainless steel, titanium, nitinol, polypropylene, polyurethane, polycarbonate, polyethylene, nylon, silicone rubber, or expanded-polytetrafluoroethylene. The material selection of threaded fixation structure 90 may be based upon whether the structure is desired to be rigid, semi-rigid, or flexible properties. Threaded fixation structure 90 may be adhered to elongated member 86 through a glue, an epoxy, welding, soldering, or any other attachment mechanism. In other embodiments, threaded fixation structure 90 may be an overmold that is fitted to a snug fit around elongated member 86. Alternatively, threaded fixation structure 90 may be integrally formed with elongated member 86, e.g., by injection molding and/or insert molding.

In addition, threaded fixation structure 90 may have a cross-sectional shape configured to assist the advancement of lead 84 through the adjacent tissue. The cross-sectional shape may generally be a triangle, but other shapes are possible. For example, the cross-sectional shape of threaded fixation structure 90 may be a rounded triangle, a semicircle, a square, a rectangle, a trapezoid, or any other shape desired by the clinician. In addition, the cross-sectional shape may be angled in a direction non-perpendicular to the outer surface of elongated member 86. For example, threaded fixation structure 90 may be tilted toward the proximal end of lead 84. In other words, the angle between the outer surface of elongated member 86 and the proximal side of threaded fixation structure 90 may be less than 90 degrees. Alternatively, the angle between the outer surface of elongated member 86 and the proximal side of threaded fixation structure 90 may be greater than 90 degrees.

Threaded fixation structure 90 may also be configured to advance through tissue at a predetermined rate or extend into the tissue a predetermined distance. The pitch of threaded fixation structure 90 may be defined by the distance lead 84 is advanced with each full 360 degree rotation of the lead, i.e., the axial distance between two peaks of the threaded fixation structure. Threaded fixation structure 90 may have a pitch between approximately 0.5 millimeters (mm) and 3 mm. In some embodiments, the pitch may be less than approximately 0.5 mm or greater than 3 mm. The height of threaded fixation structure 90 is the distance between the outer surface of elongated member 86 and the top edge of the threaded fixation structure. Generally, the height is between approximately 0.1 mm and 3 mm. However, other embodiments of threaded fixation structure 90 may include heights smaller than approximately 0.1 mm or greater than 3 mm. As threaded fixation structure 90 increases in height, the surface area of the threaded fixation structure increases as well. A larger surface area of threaded fixation structure 90 may increase the axial force lead 84 may be able to incur without allowing the lead to migrate in the direction of the axial force. In other words, a larger height of threaded fixation structure 90 may be desired in cases where lead 84 is subjected to greater movement. While threaded fixation structure 90 may have a constant height, the threaded fixation structure may increase in height as it moves towards the proximal end of the threaded fixation structure. Elongated member 62 may have an outside diameter between approximately 0.5 mm and 5 mm. The wall thickness of elongated member 62 may be between approximately 0.1 mm and 2 mm. In addition, the ratio of diameter to thread height may be between approximately 1 and 50, depending on the application of lead 60.

Implantation of all leads 60, 72, and 84, may vary depending on the target stimulation site within patient 16 or implant preferences of the clinician. For example, a sheath (shown in FIGS. 3A and 3B) may be used to cover any threaded fixation structures to allow insertion of the lead without requiring rotation of the lead. Upon positioning the lead near the stimulation site, the clinician may remove the sheath and begin rotating the lead to engage to recently exposed threaded fixation structure. Alternatively, the clinician may guide and rotate the lead through a substantial length of the insertion of the lead without the use of a sheath.

Figure 5A:
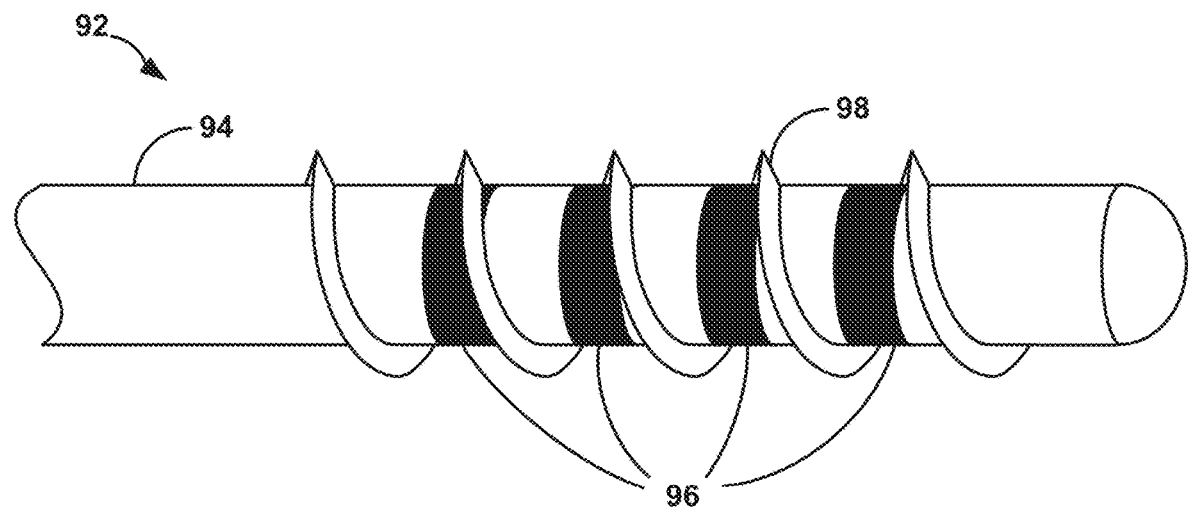
FIGS. 5A-5B are perspective drawings illustrating exemplary stimulation leads with varying threaded fixation mechanisms over electrodes of the lead.
Figure 5B:
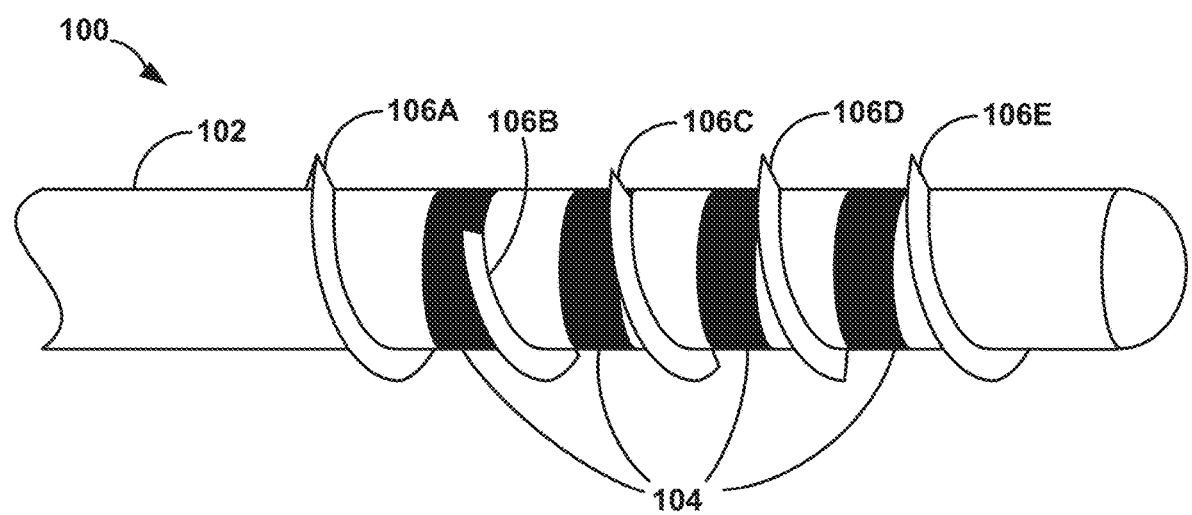

FIGS. 5A-5B are perspective drawings illustrating exemplary stimulation leads with varying threaded fixation mechanisms over electrodes of the lead. As shown in FIG. 5A, lead 92 includes elongated member 94, electrodes 96, and threaded fixation structure 98, a fixation structure. Threaded fixation structure 98 is shown to be disposed around the same portion of elongated member 94 that includes electrodes 96. In this manner, threaded fixation structure 98 is located over a portion of the surface of each electrode 96 as the threaded fixation structure rotates from the proximal end of the threaded fixation structure to the distal end of the threaded fixation structure. Utilizing threaded fixation structure 98 over electrodes 96 may provide for reduced movement of electrodes 96 with respect to the target tissue, compared to threaded fixation structures located elsewhere along the longitudinal outer surface of lead 92. Threaded fixation structure 98 may be constructed similar to and have similar physical properties of threaded fixation structure 90 of FIG. 4C. Threaded fixation structure 98 may attached to electrodes 96 with an adhesive or other bonding technique, while some embodiments may not have the threaded fixation structure attached to the electrodes.

While threaded fixation structure 98 is shown to be substantially disposed around the entire portion of elongated member 94 that includes electrodes 96, the threaded fixation structure may also be disposed further in the proximal or distal direction along the elongated member. In some embodiments, threaded fixation structure 98 may only be disposed on a portion of the surface including electrodes 96. In other words, threaded fixation structure 98 may not be disposed around all electrodes 96, e.g., the threaded fixation structure may only be disposed around the proximal two electrodes. In other embodiments, lead 92 may include threaded fixation structure 98 at locations along elongated body similar to leads 60, 72, or 84 of FIGS. 4A, 4B, and 4C, respectively.

FIG. 5B shows lead 100 that is substantially similar to lead 92 of FIG. 5A. Lead 100 includes elongated member 102, electrodes 104, and threaded fixation structures 106A, 106B, 106C, 106D and 106E (collectively "threaded fixation structures 106). Threaded fixation structures 106 are disposed at the portion of elongated member 102 which also includes electrodes 104. However, none of threaded fixation structures 106 are located over the surface of any of electrodes 104. Instead, each of threaded fixation structures 106 are only attached to elongated member 102 and stop before covering any portion of electrodes 104. In other words, threaded fixation structures 106 may be substantially similar to threaded fixation structure 98 of FIG. 5B, but have any portion of the threaded fixation structure over electrodes 96 removed. In this manner, threaded fixation structures 106 are arranged in sections to avoid interference with the electrical field produced by electrodes 104 that provides therapy to the target tissue of patient 16. Threaded fixation structures 106 may be constructed similar to and have physical properties similar to threaded fixation structure 90 of FIG. 4C. In some embodiments, one or more of threaded fixation structures 106 may be constructed of different materials to the other threaded fixation structures.

Threaded fixation structures 106B-D are located between electrodes 104, threaded fixation structure 106A is disposed proximal to electrodes 104 and threaded fixation structure 106E is disposed distal to the electrodes. In some embodiments, threaded fixation structure 106A may include more turns and be disposed along a greater proximal portion of elongated member 102. Alternatively, threaded fixation structure 106E may include more turns and be disposed along a greater distal portion of elongated member 102. In other embodiments, one or more of threaded fixation structures 106 may not be included in lead 100. For example, lead 100 may only include threaded fixation structures 106A-C. In additional embodiments, lead 100 may include threaded fixation structures at locations along elongated body similar to leads 60, 72, or 84 of FIGS. 4A, 4B, and 4C, respectively.

Figure 6:
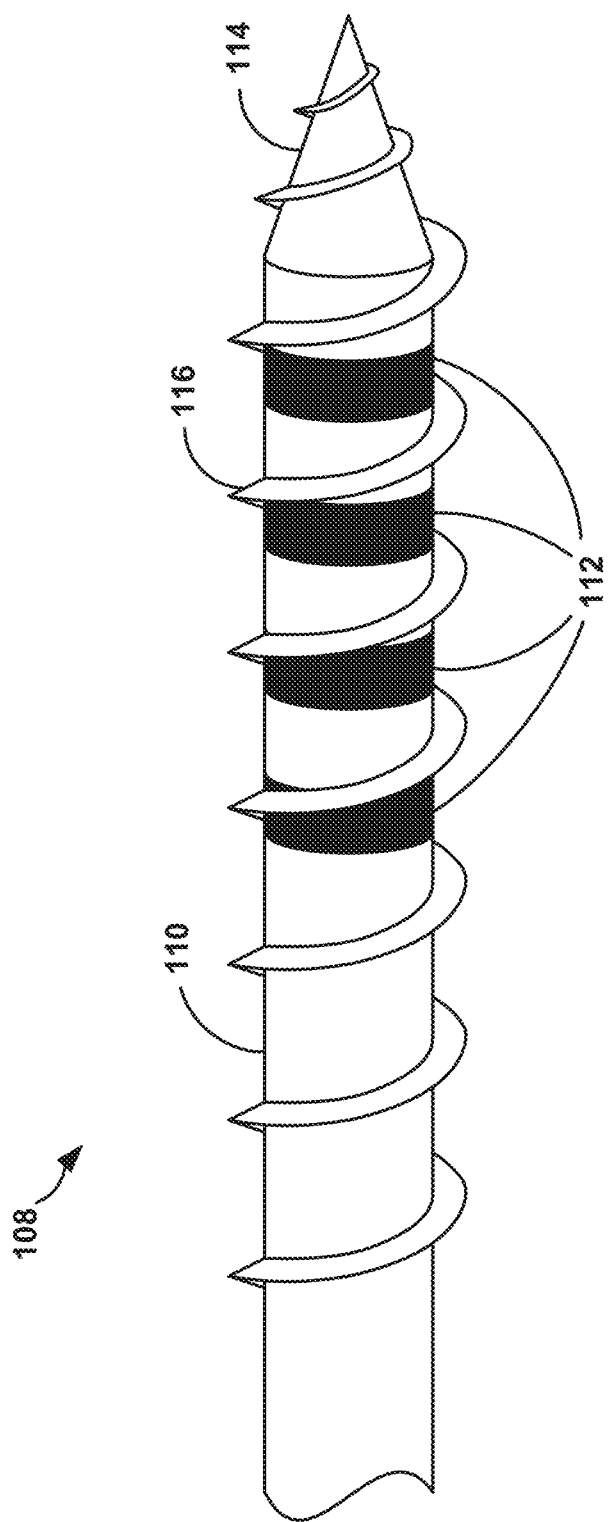
FIG. 6 is a perspective drawing illustrating an exemplary stimulation lead with threads from the distal tip to a location proximal to electrodes.

FIG. 6 is a perspective drawing illustrating lead 108 with threaded fixation structure extending from the distal end of the lead to a location proximate to electrodes 112. As shown in FIG. 6, lead 108 includes elongate member 110, electrodes 112, tapered tip 114, and threaded fixation structure 116. Threaded fixation structure begins at the distal tip of tapered tip 114 and continues to wrap around elongate member 110 past electrodes 112 to a location of the electrode member proximal to the electrodes. Lead 108 may be a combination of threaded fixation structures described with respect to leads 60, 72, 84, 92, or 100 of FIGS. 4 and 5. In addition, threaded fixation structure 116 may have similar properties to any of threaded fixation structures 70, 82, 90, 98, or 106. In other embodiments threaded fixation structure 116 may be broken into two or more threaded fixation structures at any location along tapered tip 114 or elongated member 110, including threaded fixation structures that do not cover the surface of electrodes 112. In alternative embodiments, lead 108 may include threaded fixation structures at the proximal and/or intermediate locations of elongate member 110 instead of or in addition to threaded fixation structure 116.

Figure 7:
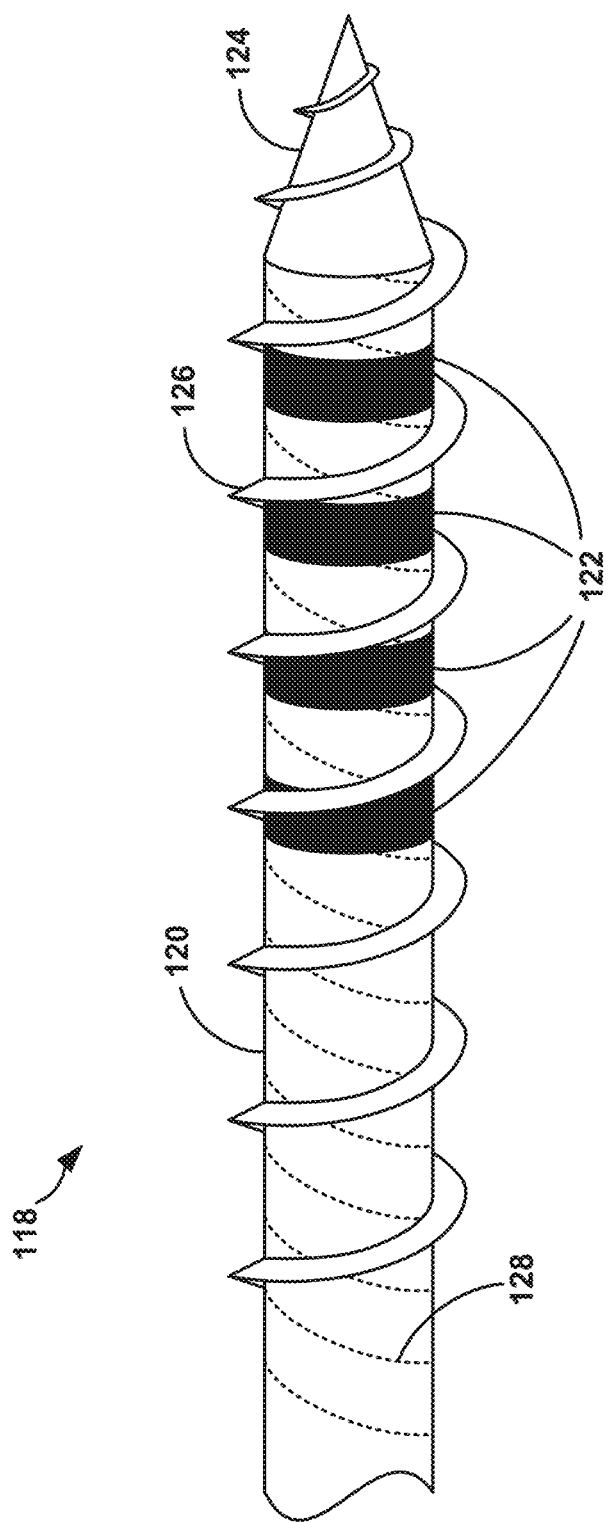
FIG. 7 is a perspective drawing illustrating an exemplary stimulation lead with torsional reinforcement members within the elongated member.

FIG. 7 is a perspective drawing illustrating lead 118 that includes a reinforcement member. Lead 118 is substantially similar to lead 108 of FIG. 6 and includes elongate member 120, electrodes 122, tapered tip 124, and threaded fixation structure 126. In contrast to lead 108, lead 118 includes helical reinforcement member 128 which resides within elongated member 120. Helical reinforcement member 128 is provided to add torsional rigidity to lead 118 which resists twisting of elongated member 120 when the clinician rotates the lead to engage threaded fixation structure 126.

Helical reinforcement member 128 may be provided in a variety of methods. First, helical reinforcement member 128 may be a metal or polymer wire. Second, helical reinforcement member 128 may be a metal or polymer ribbon that creates a substantially contiguous cylinder. Other fibers, materials, or members may be used to construct helical reinforcement member 128, in some embodiments. While helical reinforcement member 128 is shown as extending within elongate member 120 in a direction opposite threaded fixation structure 126, some embodiments may employ the helical reinforcement member in the same direction as the threaded fixation structure. Alternatively, helical reinforcement member 128 may include two helical reinforcement members in which one helical reinforcement member is arranged in one direction and the second helical reinforcement member is arranged in a second direction opposite the first direction. Helical reinforcement member 128 may extend throughout the entire length of lead 118 or only a small portion of the lead.

Figure 8A:
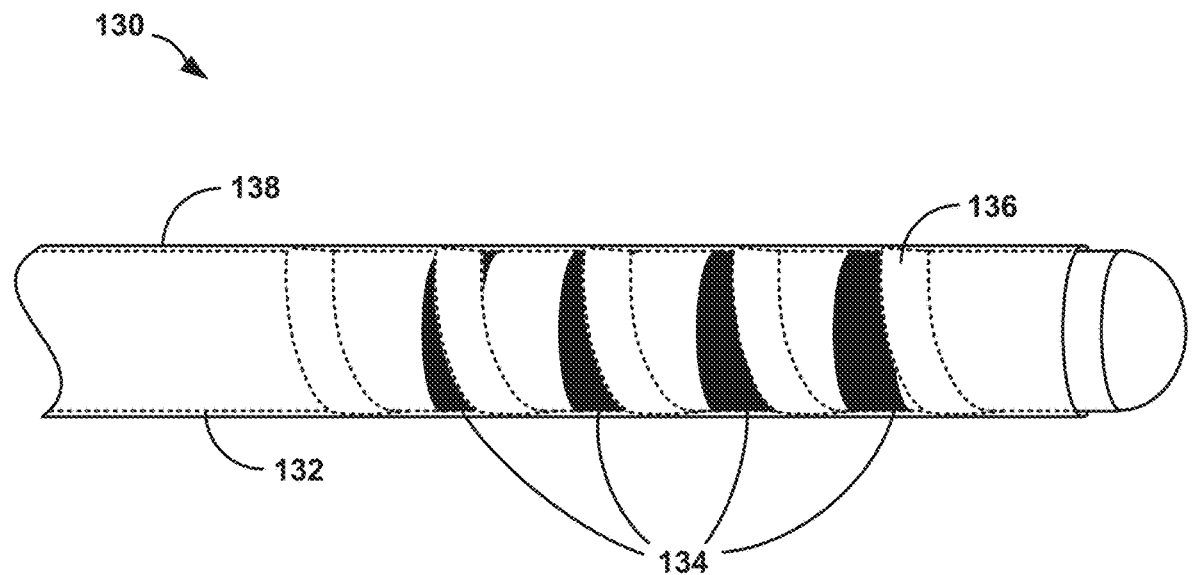
FIGS. 8A and 8B are perspective drawings illustrating exemplary stimulation leads with foldable threads.
Figure 8B:
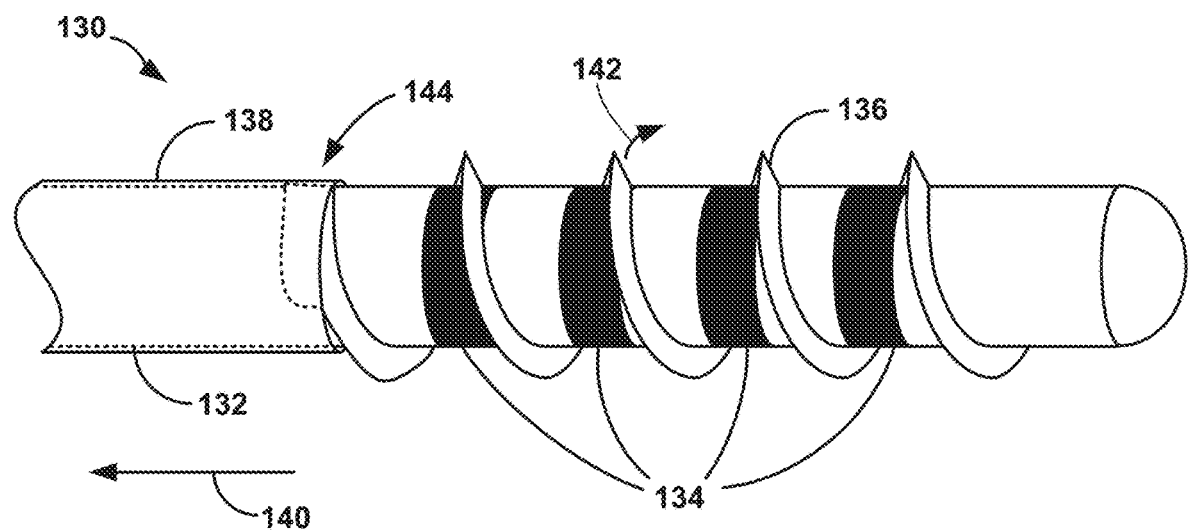

FIGS. 8A and 8B are perspective drawings illustrating exemplary stimulation leads with foldable threads. FIG. 8A illustrates lead 130 prior to the removal of sheath 138. Lead 130 includes elongated member 132, electrodes 134, threaded fixation structure 136, and sheath 138. Lead 130 may be similar to any of leads 60, 72, 84, 92, 100, 108 or 118; however, threaded fixation structure 136 is foldable, or compliant, such that sheath 138 prevents the threaded fixation structure from extending away from elongated member 132. While threaded fixation structure 136 is shown to be disposed around the portion of elongated member 132 that includes electrodes 134, the threaded fixation structure may be disposed at any portion of the elongated member as described herein.

Sheath 138 is provided to facilitate implantation of lead 130. With sheath 138 covering elongated member 132 and collapsing threaded fixation structure 136, the diameter of lead 130 is smaller to allow the clinician to push the lead through a lead introducer (not shown) or through tissue of patient 16. Once the clinician inserts lead 130 to the desired position, sheath 138 is removed to expose threaded fixation structure 136 to the adjacent tissue. Threaded fixation structure 136 extends away from the outer surface of elongated member 132 to the originally formed threaded fixation structure dimensions. Rotating lead 130 may help threaded fixation structure 136 to extend away from the surface of elongated member 132 and engage the surrounding tissue. The extended angle of threaded fixation structure 136 may be less than 90 degrees between the outer surface of elongated member 132 and the proximal surface of the threaded fixation structure. While threaded fixation structure 136 is foldable towards the proximal end of lead 130, the threaded fixation structure may be foldable towards the distal end of the lead in other embodiments.

Threaded fixation structure 136 may be constructed of any bendable, pliable, elastic, or superelastic material that is biocompatible. For example, a polymer such as expanded-polytetrafluoroethylene or a shape memory metal alloy such as nitinol may be used to construct threaded fixation structure 136. Sheath 138 may be constructed of a thin polymer membrane that may slide over the surface of elongated member 132 and threaded fixation structure 136 while maintaining sufficient circumferential stiffness that retains the threaded fixation structure before deployment. Sheath 138 may be initially configured to cover elongated member 132 and threaded fixation structure 136 by sliding the sheath from the distal end of lead 130 to the proximal end of the lead. Alternatively, sheath 138 may loosely cover lead 130 and be heated to shrink the circumference of the sheath and collapse threaded fixation structure 136.

FIG. 8B shows lead 130 with sheath 138 being removed in the proximal direction of arrow 140. The distal portion of threaded fixation structure 136 has already extended away from elongated member 132 in the direction of arrow 142. The proximal portion of threaded fixation structure, indicated by arrow 144, is still restricted by sheath 138 that has not been fully removed. Once sheath 138 is fully removed from lead 130, the clinician may rotate the lead to engage threaded fixation structure 136 with the adjacent tissue. In addition, once sheath 138 is removed from lead 130, the clinician may not be able to slide the sheath back over threaded fixation structure 136.

In alternative embodiments, sheath 138 may not be necessary for threaded fixation structure 136 to fold down against elongated member 132. Threaded fixation structure 136 may fold down from force from adjacent tissue when the clinician inserts lead 130 into patient 16. When lead 130 is properly positioned, the clinician may pull back on the lead to cause threaded fixation structure 136 to engage with the adjacent tissue and extend the threaded fixation structure away from elongated member 132. The clinician can then begin to rotate lead 130 to screw the lead into the tissue and secure electrodes 134 to the desired location.

Figure 9:
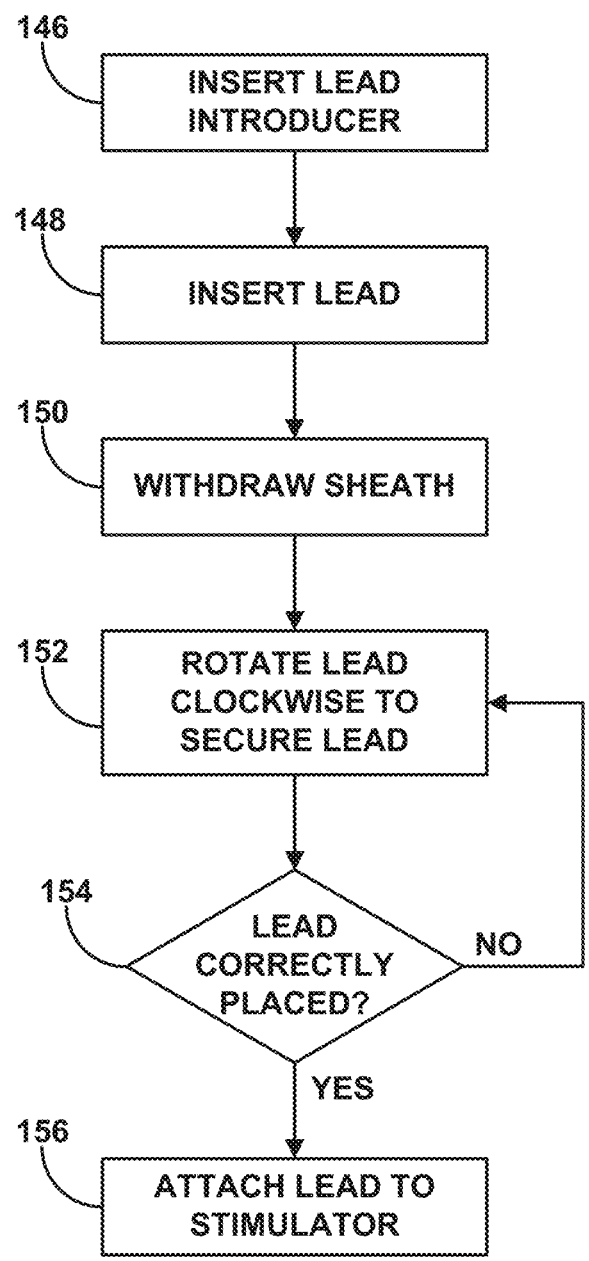
FIG. 9 is a flow diagram illustrating an exemplary process for securing a threaded lead to a tissue of a patient.

FIG. 9 is a flow diagram illustrating an exemplary process for securing a threaded lead to a tissue of a patient. Any of leads 60, 72, 84, 92, 100, 108 or 118, or 130 may be implanted with this procedure, but lead 60 will be used as an example. The clinician beings by inserting the lead introducer into the target stimulation site of patient 16 (146). Next, the clinician inserts lead 60 into the lead introducer until the lead is positioned correctly (148). The clinician then withdraws the sheath that covers lead 60 (150) and rotates the lead in the direction of threaded fixation structure 68, e.g., clockwise, to secure the lead at the target tissue (152). If lead 60 is not correctly placed (154), the clinician continues to rotate the lead (152). If lead 60 is positioned correctly (154), the clinician may attach the proximal end of the lead to the stimulator and proceed with beginning therapy (156).

In some embodiments, the clinician may not need to remove a sheath to expose the threaded fixation structure. In other embodiments, the clinician may require a keyed stylet or other device that engages into the distal end of the lead and locks into interior grooves or teeth to facilitate the rotation of the lead and engagement of the threaded fixation structure. Alternatively, the stylet may be inserted through a channel extending within lead 60 that attaches to grooves, slots, or teeth near the proximal end of the lead to facilitate lead rotation that engages the threaded fixation structure to the adjacent tissue.

Figure 10:
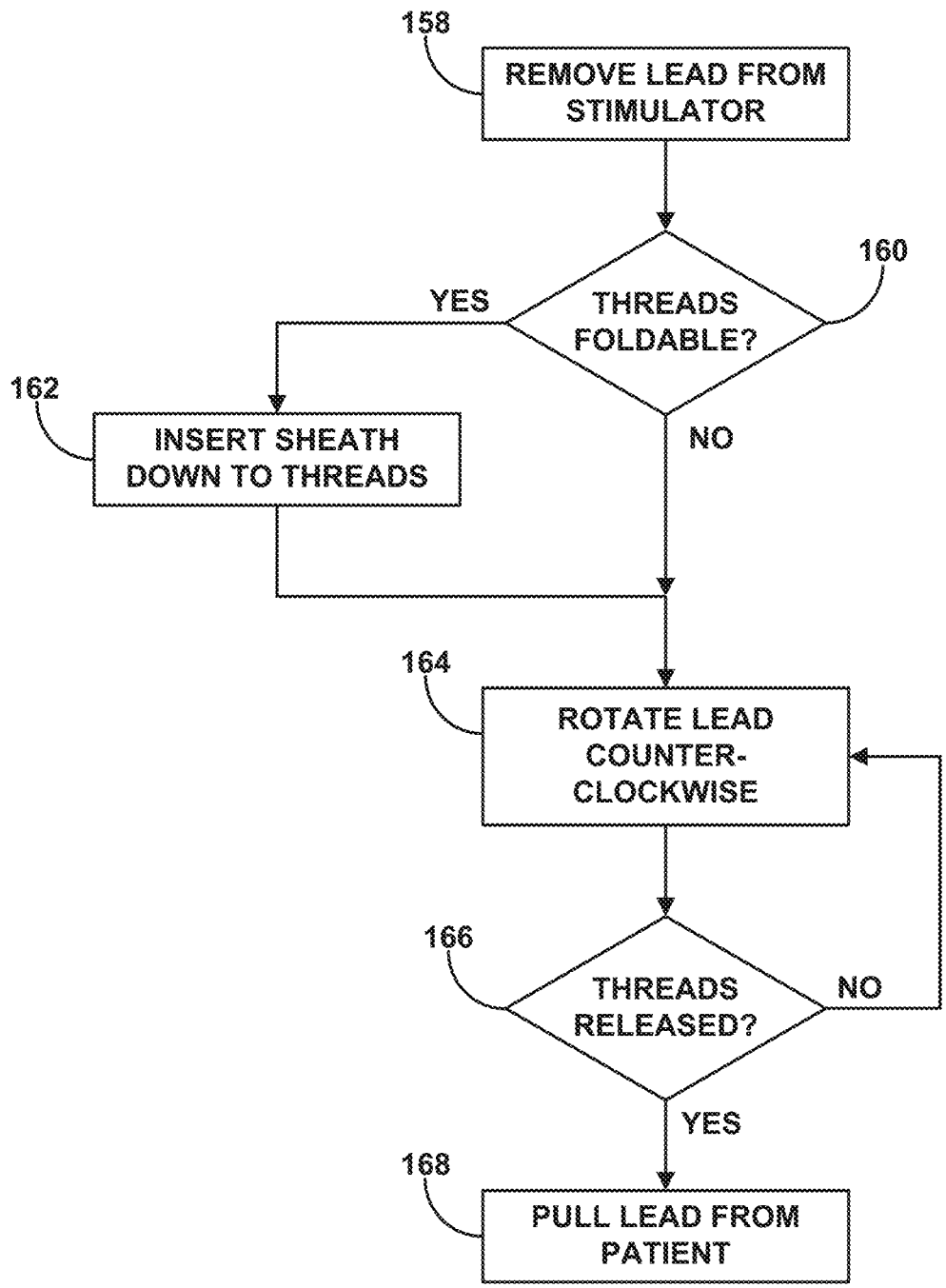
FIG. 10 is a flow diagram illustrating an exemplary process for removing a threaded lead from a tissue of a patient.

FIG. 10 is a flow diagram illustrating an exemplary process for removing a threaded lead from a tissue of a patient. Any of leads 60, 72, 84, 92, 100, 108 or 118, or 130 may be implanted with this procedure, but lead 60 will be used as an example. After stimulation therapy has been completed or lead 60 needs to be removed for any other reason, the clinician may ready patient 16 for removal of the lead from stimulator 12 (158). If the threaded fixation structure is foldable (160), the clinician inserts a sheath down to the proximal end of the threaded fixation structure (162). If the threaded fixation structure of lead 60 is not foldable, or the sheath has been inserted to the foldable threads, the clinician begins to rotate the lead in the opposite direction of the threaded fixation structure, e.g., counter-clockwise (164). If the threaded fixation structure is not released from tissue (166), the clinician continues to rotate lead 60 (164). If the threaded fixation structure has been released from tissue (166), the clinician may pull lead 60 from patient 16 (168). Releasing the threaded fixation structure from the tissue may include either backing the threaded fixation structure into the sheath such that the structure folds under the sheath or rotating the lead enough that the threaded fixation structure is free from being engaged from any tissue of patient 16.

Similar to FIG. 9, some embodiments may require that the clinician use a keyed stylet or other device that engages into the distal end of the lead and locks into interior grooves or teeth to facilitate the rotation of the lead and disengagement of the threaded fixation structure. Alternatively, the stylet may be inserted through a channel extending within lead 60 that attaches to grooves, slots, or teeth near the proximal end of the lead to facilitate lead rotation that disengages the threaded fixation structure from the adjacent tissue.

Figure 11:
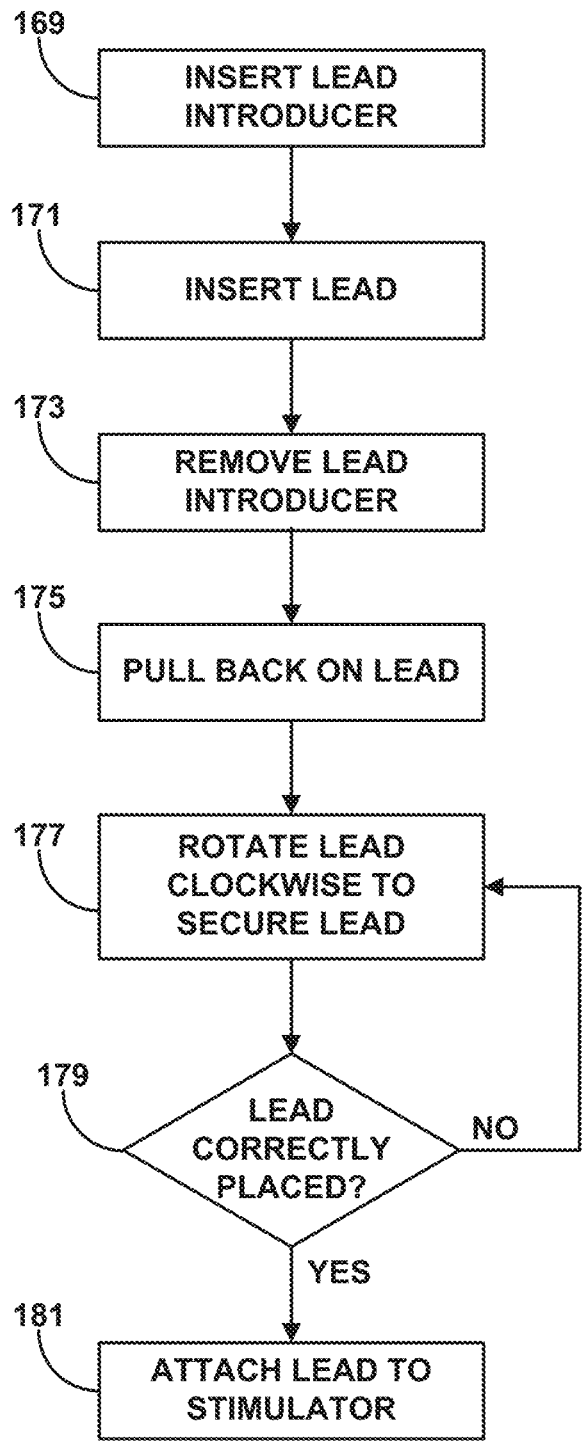
FIG. 11 is a flow diagram illustrating an exemplary process for securing a lead with folding threads to a tissue of a patient.

FIG. 11 is a method of implanting a lead in patient 12 with a different threaded fixation structure than the leads implanted in with the technique of FIG. 9. Any of leads 60, 72, 84, 92, 100, 108 or 118, or 130 with a foldable threaded fixation structure may be implanted with this procedure, but lead 130 will be used as an example. The clinician beings by inserting the lead introducer into the target stimulation site of patient 16 (169), which causes threaded fixation structure 136 to fold down against the surface of lead 130. Next, the clinician inserts lead 130 into the lead introducer until the lead is positioned correctly (171). The clinician then removes the lead introducer that covers lead 130 (173) and pulls back on the lead to engage, or extend, the folded threaded fixation structure with the adjacent tissue (175). The clinician then rotates the lead in the direction of threaded fixation structure 136, e.g., clockwise, to secure the lead at the target tissue (177). If lead 130 is not correctly placed (179), the clinician continues to rotate the lead (177). If lead 130 is positioned correctly (179), the clinician may attach the proximal end of the lead to the stimulator and proceed with beginning therapy (181).

In some embodiments, the clinician may be able to insert lead 130 directly into patient 16 without the use of a lead introducer. In this case, foldable threaded fixation structure 136 folds down with the force of the adjacent tissue as lead 130 is inserted into patient 16. In other embodiments, the clinician may require a keyed stylet or other device that engages into the distal end of the lead and locks into interior grooves or teeth to facilitate the rotation of the lead and engagement of the threaded fixation structure. Alternatively, the stylet may be inserted through a channel extending within lead 130 that attaches to grooves, slots, or teeth near the proximal end of the lead to facilitate lead rotation that engages the threaded fixation structure to the adjacent tissue.

Figure 12A:
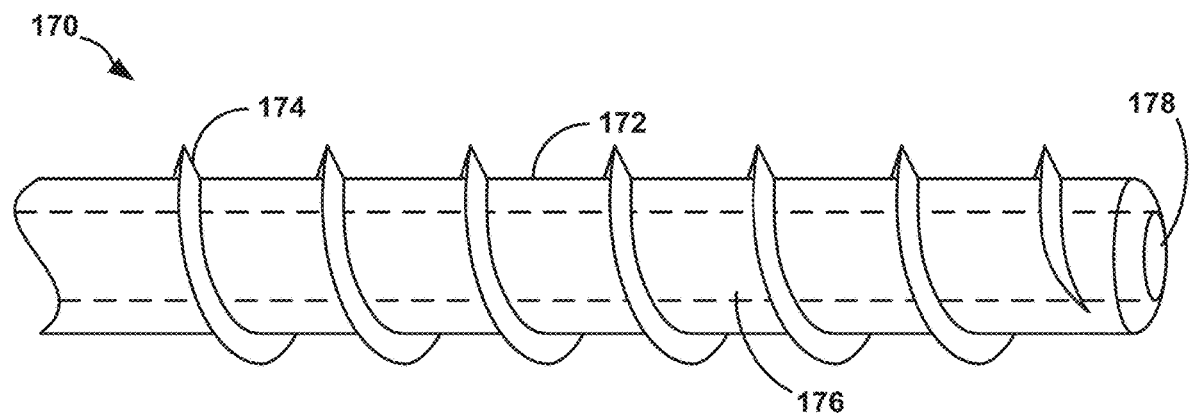
FIGS. 12A and 12B are perspective drawings illustrating exemplary medical catheters with a helical threaded structure.
Figure 12B:
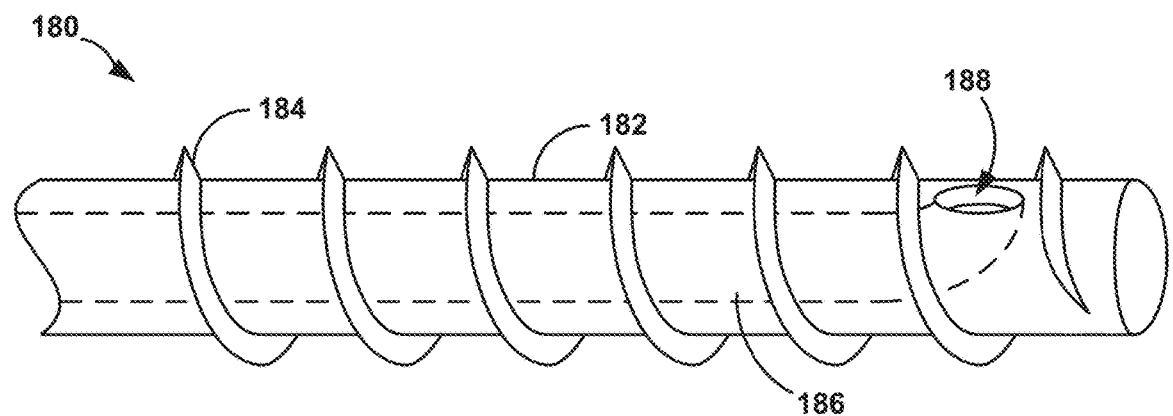

FIGS. 12A and 12B are perspective drawings illustrating exemplary medical catheters with a helical threaded structure. Threaded fixation structures 174 and 184 may be similar to the threaded fixation structures of any of leads 60, 72, 84, 92, 100, 108 or 118, or 130. However, a conduit is used to deliver a therapeutic agent to the tissue instead of electrodes that deliver stimulation. FIG. 12A shows lead 170 that includes elongated member 172, threaded fixation structure 174, conduit 176, and exit port 178. Threaded fixation structure 174 is disposed about the outer surface of elongated member 172 at the distal end of the elongated body. A drug pump may be attached to the proximal end of lead 170 for delivering a therapeutic agent through conduit 176 and out of exit port 178 into the adjacent target tissue. Conduit 176 resides within elongated member 172, and may or may not have a common central axis to the elongated member. In other embodiments, more than one threaded fixation structure 174 may be provided to secure the location of lead 170 and ensure that the therapeutic agent is delivered to the appropriate tissue of patient 16.

FIG. 12B shows lead 180 which is similar to lead 170 of FIG. 12A. Lead 180 includes elongated body 182, threaded fixation structure 184, conduit 186, and exit port 188. Exit port 188 is disposed on a longitudinal outer surface of elongated member 182, within threaded fixation structure 184. Conduit 186 resided within elongated member 182, and may or may not have a common central axis with the elongated member. In other embodiments, exit port 188 may be located outside of threaded fixation structure 184 either distal to or proximal to the threaded fixation structure. In alternative embodiments, conduit 186 may be in fluidic communication with more than one exit port, where the multiple exit ports are located at various longitudinal or circumferential positions of elongated member 182 or in the axial surface of the elongated member. In addition, lead 180 may include multiple conduits within elongated member 182.

Figure 13A:
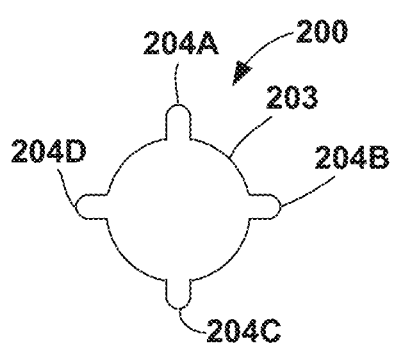
FIGS. 13A and 13B are cross-sectional end views of a keyed stylet and reciprocally keyed medical lead.
Figure 13B:
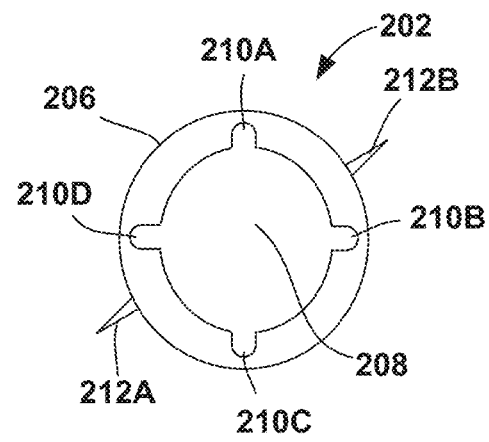

FIGS. 13A and 13B are cross-sectional end views of a keyed stylet 200 and a reciprocally keyed medical lead 202. As discussed previously, rotational movement of a lead may be accomplished by simply rotating the lead body. In some embodiments, however, it may be desirable to rotate the lead body with the aid of a stylet inserted in an inner lumen of the lead body. For example, a stylet may provide added structural integrity relative to a flexible lead. The stylet may be sized to frictionally engaged the inner wall of the inner lumen such that rotation of the stylet causes rotation of the lead body. Alternatively, the stylet and the lead body may be formed with a reciprocal key structure, such as any combination of slots, grooves, teeth, ribs, rails, or the like.

In the example of FIGS. 13A and 13B, stylet 200 includes a stylet body 203 with multiple teeth 204A-204D. The teeth may run longitudinally substantially the entire length of the stylet body 203, or be provided only near a distal end of the stylet body, e.g., over the last 2 to 6 centimeters at the distal end of the stylet. In either case, teeth 204A-204D may be sized and shaped to engage reciprocal grooves 210A-210D in a lead body 206 of lead 202. The grooves 210A-210D may be formed by molding, extruding, scribing or other techniques. In any event, teeth 204A-204D engage corresponding grooves 210A-210D so that the teeth can bear against the grooves to transmit rotational force from stylet 200 to lead 202.

Also shown in FIG. 13B are representative portions 212A, 212B of a threaded fixation structure. Any thread fixation structure, as described herein, may be combined with a lead 202 including slots, grooves, or the like. Moreover, the number of slots or grooves may be subject to wide variation. Also, in some embodiments, lead 202 may include teeth while stylet 200 includes grooves. The exact combination, arrangement, size, and number of slots, grooves, teeth or the like is subject to variation provided the lead 202 and stylet 200 include reciprocal structure to impart rotational movement from the stylet to the lead.

Alternative to keyed stylet 200, a cannula device that is configured to fit around the outside of the lead may be used to rotate the lead and engage the threaded fixation structure. The cannula device may be circumferentially locked to the lead via one or more slots, grooves, teeth, ribs, rails, or the like, disposed on the outside of the elongated member. In some embodiments, the cannula device may use a friction fit to lock to the lead. In either case, the cannula device may be slid down to the proximal end of the threaded fixation structure or some other location of the lead that still facilitates rotation of the lead.

A lead including threaded fixation may be useful for various electrical stimulation systems. For example, the lead may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In addition, the helical fixation described herein may also be useful for fixing a catheter, such as a drug deliver catheter, proximate to a target drug delivery site.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems and leads for stimulation, as described herein. Also, the leads described herein may have a variety of stimulation applications, as well as possible applications in other electrical stimulation contexts, such as delivery of cardiac electrical stimulation, including paces, pulses, and shocks.

Many embodiments of the invention have been described. Various modifications may be made without departing from the scope of the claims. These and other embodiments are within the scope of the following claims.

The invention claimed is:

1. A medical lead for treating incontinence, the medical lead comprising:
    an elongated member having a proximal end and a distal end, the proximal end being configured to electrically and mechanically couple to a medical device comprising stimulation circuitry;
    four stimulation electrodes configured to deliver electrical stimulation generated by the medical device to a sacral nerve of a patient when the elongated member is electrically and mechanically coupled to the medical device;
    a plurality of fixation structures arranged to form a helical pattern around a portion of an outer surface of the elongated member and configured to engage tissue within the patient, wherein the helical pattern is proximal of the four electrodes, and wherein each fixation structure of the plurality of fixation structures has a free end configured to be spaced from the elongated member; and
    a sheath configured to cover at least the portion of the outer surface of the elongated member including the plurality of fixation structures, wherein the plurality of fixation structures is configured to fold towards the elongated member when restrained by the sheath, and wherein the free end of each fixation structure of the plurality of fixation structures is configured to be deployed as the sheath is removed from the plurality of fixation structures to anchor the lead.

2. The medical lead of claim 1, wherein the plurality of fixation structures is disposed proximal of all stimulation electrodes disposed along the elongated member, the all stimulation electrodes comprising the four stimulation electrodes.

3. The medical lead of claim 1, wherein each fixation structure of the plurality of fixation structures comprises, opposite of the free end, a secured end attached to the elongated member.

4. The medical lead of claim 1, wherein the sheath is configured to collapse the plurality of fixation structures to reduce a diameter of the medical lead until the sheath is removed from the plurality of fixation structures.

5. The medical lead of claim 1, wherein the plurality of fixation structures is a first plurality of fixation structures and the helical pattern is a first helical pattern, further comprising a second plurality of fixation structures arranged to form a second helical pattern and disposed distal of the four electrodes.

6. The medical lead of claim 1, wherein the plurality of fixation structures comprise polyurethane.

7. The medical lead of claim 1, wherein each fixation structure of the plurality of fixation structures have a height between 0.1 mm and 3 mm from an outer surface of the elongated member.

8. The medical lead of claim 1, wherein each stimulation electrode of the four stimulation electrodes comprises a ring electrode disposed at a respective location along the outer surface of the elongated member.

9. The medical lead of claim 1, wherein the plurality of fixation structures is configured to fold towards the distal end of the elongated member when restrained by the sheath.

10. The medical lead of claim 1, wherein the plurality of fixation structures are configured to fold towards the proximal end of the elongated member when restrained by the sheath.

11. The medical lead of claim 1, wherein the plurality of fixation structures are configured to extend away from the elongated member in response to removal of the sheath.

12. The medical lead of claim 1, wherein the elongated member defines an outside diameter between 0.5 mm and 5 mm.

13. A method for treating incontinence, the method comprising:
   inserting a medical lead to a location proximate to a sacral nerve of a patient, wherein the medical lead comprises:
      an elongated member having a proximal end and a distal end, the proximal end being configured to electrically couple to a medical device comprising a stimulation circuitry;
      four stimulation electrodes disposed closer to the distal end of the elongated member than the proximal end of the elongated member, the four stimulation electrodes being configured to deliver electrical stimulation generated by the medical device to the sacral nerve of the patient when the elongated member is electrically and mechanically coupled to the medical device; and
      a plurality of fixation structures arranged to form a helical pattern around a portion of an outer surface of the elongated member and configured to engage tissue within the patient, wherein the helical pattern is disposed proximal of the four stimulation electrodes disposed along the elongated member;
   removing a sheath from the medical lead to deploy the plurality of fixation structures as the sheath is removed from the plurality of fixation structures to anchor the lead in tissue of the patient, wherein the sheath is configured to deflect and cover the plurality of fixation structures, and wherein the plurality of fixation structures are configured to fold towards the elongated member when restrained by the sheath; and
   attaching the medical lead to the medical device.

14. The method of claim 13, wherein inserting the medical lead comprises rotating the medical lead.

15. The method of claim 13, wherein removing the sheath from the medical lead comprises withdrawing the sheath from the medical lead to deploy the plurality of fixation structures as the sheath is withdrawn from the plurality of fixation structures to anchor the lead in the tissue of the patient.

16. The method of claim 13, wherein the plurality of fixation structures is attached to the elongated member.

17. The method of claim 13, wherein the plurality of fixation structures comprises a polymer.

18. A system for treating incontinence, the system comprising:
   a medical lead comprising:
      an elongated member having a proximal end portion with a plurality of electrical contacts and a distal end, the elongated member defining a central axis;
      four stimulation electrodes configured to deliver electrical stimulation generated by a medical device to a sacral nerve of a patient, the four stimulation electrodes being equally spaced along the central axis;
      a plurality of conductor wires between the four electrodes and the plurality of electrical contacts;
      a plurality of polymer fixation structures arranged in a helical pattern around a portion of the elongated member and configured to engage tissue within the patient, each fixation structure of the plurality of polymer fixation structures having a free end, each fixation structure of the plurality of polymer fixation structures having a deployed height between 0.1 mm and 3 mm from an outer surface of the elongated member to the free end, wherein the helical pattern is proximal from the four stimulation electrodes;
      a visual marker associated with the medical lead;
   a sheath configured to cover at least the plurality of polymer fixation structures, wherein the plurality of polymer fixation structures are configured to fold towards the elongated member when restrained by the sheath, and wherein the plurality of polymer fixation structures are configured to be deployed as the sheath is removed from the plurality of fixation structures to anchor the lead;
   a stimulator having a rechargeable battery, the stimulator being configured to deliver electrical stimulation therapy to the sacral nerve of the patient via at least one electrode of the four stimulation electrodes of the medical lead within the patient, the proximal end portion of the elongated member being configured to mechanically couple to the stimulator;
   a clinician programmer configured to program stimulation therapy for the patient; and
   a patient device configured to control stimulation therapy from the stimulator.

19. The system of claim 18, wherein each stimulation electrode of the four stimulation electrodes comprises a cylindrical stimulation electrode.

20. The system of claim 18, wherein the plurality of fixation structures is constructed from polyurethane and configured to fold towards the proximal end of the elongated member when restrained by the sheath.

21. The system of claim 18, wherein the plurality of fixation structures is configured to extend away from the elongated member in response to removal of the sheath.

22. A medical lead for treating incontinence, the medical lead comprising:
 an elongated member having a proximal end and a distal end, the proximal end having four electrical contacts, the electrical contacts being configured to electrically couple the medical lead to a medical device comprising stimulation circuitry;
 four stimulation electrodes disposed closer to the distal end of the elongated member than the proximal end of the elongated member, the four stimulation electrodes being configured to deliver electrical stimulation generated by the medical device to a sacral nerve of a patient when the elongated member is electrically and mechanically coupled to the medical device;
 a plurality of discontinuous fixation structures disposed in a helical shape around a portion of an outer surface of the elongated member and configured to engage tissue within the patient, wherein the helical shape is proximal from the four electrodes, and wherein each fixation structure of the plurality of discontinuous fixation structures has a free end configured to be spaced from the elongated member; and
 a sheath configured to cover at least the portion of the outer surface of the elongated member including the helical shape, wherein the plurality of discontinuous fixation structures are configured to fold towards the elongated member when restrained by the sheath, and wherein the plurality of discontinuous fixation structures are configured to be deployed as the sheath is removed from the plurality of fixation structures to anchor the lead.

* * * * *